United States Patent
Kovatchev et al.

(10) Patent No.: US 10,194,850 B2
(45) Date of Patent: Feb. 5, 2019

(54) ACCURACY OF CONTINUOUS GLUCOSE SENSORS

(71) Applicants: ABBOTT DIABETES CARE INC., Alameda, CA (US); UNIVERSITY OF VIRGINIA PATENT FOUNDATION, Charlottesville, VA (US)

(72) Inventors: Boris P. Kovatchev, Charlottesville, VA (US); Christopher R. King, Chicago, IL (US)

(73) Assignee: ABBOTT DIABETES CARE INC., Alameda, CA (US)

(*) Notice: Subject to any disclaimer, the term of this patent is extended or adjusted under 35 U.S.C. 154(b) by 645 days.

(21) Appl. No.: 14/799,329

(22) Filed: Jul. 14, 2015

(65) Prior Publication Data
US 2016/0007890 A1    Jan. 14, 2016

Related U.S. Application Data

(63) Continuation of application No. 12/065,257, filed as application No. PCT/US2006/033724 on Aug. 29, 2006.

(60) Provisional application No. 60/815,191, filed on Jun. 20, 2006, provisional application No. 60/713,203, filed on Aug. 31, 2005.

(51) Int. Cl.
A61B 5/00     (2006.01)
A61B 5/1495   (2006.01)
A61B 5/145    (2006.01)

(52) U.S. Cl.
CPC ........ *A61B 5/1495* (2013.01); *A61B 5/14532* (2013.01); *A61B 5/7275* (2013.01); *A61B 5/7278* (2013.01)

(58) Field of Classification Search
CPC .................. A61B 5/1495; A61B 5/14532
See application file for complete search history.

(56) References Cited

U.S. PATENT DOCUMENTS

| | | |
|---|---|---|
| 3,581,062 A | 5/1971 | Aston |
| 3,926,760 A | 12/1975 | Allen et al. |
| 3,949,388 A | 4/1976 | Fuller |
| 3,960,497 A | 6/1976 | Acord et al. |
| 3,978,856 A | 9/1976 | Michel |
| 4,036,749 A | 7/1977 | Anderson |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |

(Continued)

FOREIGN PATENT DOCUMENTS

| | | |
|---|---|---|
| EP | 0098592 | 1/1984 |
| EP | 0127958 | 12/1984 |

(Continued)

OTHER PUBLICATIONS

Armour, J. C., et al., "Application of Chronic Intravascular Blood Glucose Sensor in Dogs", *Diabetes*, vol. 39, 1990, pp. 1519-1526.

(Continued)

*Primary Examiner* — Christian Jang
(74) *Attorney, Agent, or Firm* — One LLP

(57) ABSTRACT

A method, apparatus, and a kit are capable of improving accuracy of CGS devices using dynamic outputs of continuous glucose sensors.

16 Claims, 11 Drawing Sheets

(56) References Cited

U.S. PATENT DOCUMENTS

| | | |
|---|---|---|
| 4,344,438 A | 8/1982 | Schultz |
| 4,349,728 A | 9/1982 | Phillips et al. |
| 4,373,527 A | 2/1983 | Fischell |
| 4,392,849 A | 7/1983 | Petre et al. |
| 4,425,920 A | 1/1984 | Bourland et al. |
| 4,441,968 A | 4/1984 | Emmer et al. |
| 4,462,048 A | 7/1984 | Ross |
| 4,478,976 A | 10/1984 | Goertz et al. |
| 4,494,950 A | 1/1985 | Fischell |
| 4,509,531 A | 4/1985 | Ward |
| 4,527,240 A | 7/1985 | Kvitash |
| 4,538,616 A | 9/1985 | Rogoff |
| 4,545,382 A | 10/1985 | Higgins et al. |
| 4,619,793 A | 10/1986 | Lee |
| 4,671,288 A | 6/1987 | Gough |
| 4,703,756 A | 11/1987 | Gough et al. |
| 4,711,245 A | 12/1987 | Higgins et al. |
| 4,731,051 A | 3/1988 | Fischell |
| 4,731,726 A | 3/1988 | Allen, III |
| 4,749,985 A | 6/1988 | Corsberg |
| 4,757,022 A | 7/1988 | Shults et al. |
| 4,759,366 A | 7/1988 | Callaghan |
| 4,777,953 A | 10/1988 | Ash et al. |
| 4,779,618 A | 10/1988 | Mund et al. |
| 4,854,322 A | 8/1989 | Ash et al. |
| 4,871,351 A | 10/1989 | Feingold |
| 4,890,620 A | 1/1990 | Gough |
| 4,925,268 A | 5/1990 | Iyer et al. |
| 4,947,845 A | 8/1990 | Davis |
| 4,953,552 A | 9/1990 | DeMarzo |
| 4,986,271 A | 1/1991 | Wilkins |
| 4,995,402 A | 2/1991 | Smith et al. |
| 5,000,180 A | 3/1991 | Kuypers et al. |
| 5,002,054 A | 3/1991 | Ash et al. |
| 5,019,974 A | 5/1991 | Beckers |
| 5,050,612 A | 9/1991 | Matsumura |
| 5,055,171 A | 10/1991 | Peck |
| 5,068,536 A | 11/1991 | Rosenthal |
| 5,077,476 A | 12/1991 | Rosenthal |
| 5,082,550 A | 1/1992 | Rishpon et al. |
| 5,106,365 A | 4/1992 | Hernandez |
| 5,113,869 A | 5/1992 | Nappholz et al. |
| 5,122,925 A | 6/1992 | Inpyn |
| 5,135,004 A | 8/1992 | Adams et al. |
| 5,148,812 A | 9/1992 | Verrier et al. |
| 5,165,407 A | 11/1992 | Wilson et al. |
| 5,199,428 A | 4/1993 | Obel et al. |
| 5,202,261 A | 4/1993 | Musho et al. |
| 5,203,326 A | 4/1993 | Collins |
| 5,204,264 A | 4/1993 | Kaminer et al. |
| 5,210,778 A | 5/1993 | Massart |
| 5,231,988 A | 8/1993 | Wernicke et al. |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,313,953 A | 5/1994 | Yomtov et al. |
| 5,320,715 A | 6/1994 | Berg |
| 5,320,725 A | 6/1994 | Gregg et al. |
| 5,322,063 A | 6/1994 | Allen et al. |
| 5,328,460 A | 7/1994 | Lord et al. |
| 5,330,634 A | 7/1994 | Wong et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,365,426 A | 11/1994 | Siegel et al. |
| 5,372,427 A | 12/1994 | Padovani et al. |
| 5,376,070 A | 12/1994 | Purvis et al. |
| 5,379,238 A | 1/1995 | Stark |
| 5,384,547 A | 1/1995 | Lynk et al. |
| 5,390,671 A | 2/1995 | Lord et al. |
| 5,391,250 A | 2/1995 | Cheney, II et al. |
| 5,400,795 A | 3/1995 | Murphy et al. |
| 5,408,999 A | 4/1995 | Singh et al. |
| 5,411,647 A | 5/1995 | Johnson et al. |
| 5,425,749 A | 6/1995 | Adams |
| 5,425,868 A | 6/1995 | Pedersen |
| 5,431,160 A | 7/1995 | Wilkins |
| 5,431,921 A | 7/1995 | Thombre |
| 5,438,983 A | 8/1995 | Falcone |
| 5,462,645 A | 10/1995 | Albery et al. |
| 5,472,317 A | 12/1995 | Field et al. |
| 5,489,414 A | 2/1996 | Schreiber et al. |
| 5,497,772 A | 3/1996 | Schulman et al. |
| 5,505,828 A | 4/1996 | Wong et al. |
| 5,507,288 A | 4/1996 | Bocker et al. |
| 5,509,410 A | 4/1996 | Hill et al. |
| 5,514,718 A | 5/1996 | Lewis et al. |
| 5,520,191 A | 5/1996 | Karlsson et al. |
| 5,531,878 A | 7/1996 | Vadgama et al. |
| 5,532,686 A | 7/1996 | Urbas et al. |
| 5,543,326 A | 8/1996 | Heller et al. |
| 5,568,400 A | 10/1996 | Stark et al. |
| 5,568,806 A | 10/1996 | Cheney, II et al. |
| 5,569,186 A | 10/1996 | Lord et al. |
| 5,582,184 A | 12/1996 | Erickson et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,628,310 A | 5/1997 | Rao et al. |
| 5,628,890 A | 5/1997 | Nigel et al. |
| 5,634,468 A | 6/1997 | Platt et al. |
| 5,640,954 A | 6/1997 | Pfeiffer et al. |
| 5,653,239 A | 8/1997 | Pompei et al. |
| 5,660,163 A | 8/1997 | Schulman et al. |
| 5,665,222 A | 9/1997 | Heller et al. |
| 5,707,502 A | 1/1998 | McCaffrey et al. |
| 5,711,001 A | 1/1998 | Bussan et al. |
| 5,711,861 A | 1/1998 | Ward et al. |
| 5,720,295 A | 2/1998 | Greenhut et al. |
| 5,724,030 A | 3/1998 | Urbas et al. |
| 5,733,259 A | 3/1998 | Valcke et al. |
| 5,735,285 A | 4/1998 | Albert et al. |
| 5,741,211 A | 4/1998 | Renirie et al. |
| 5,749,907 A | 5/1998 | Mann |
| 5,771,891 A | 6/1998 | Gozani |
| 5,772,586 A | 6/1998 | Heinonen et al. |
| 5,785,660 A | 7/1998 | van Lake et al. |
| 5,791,344 A | 8/1998 | Schulman et al. |
| 5,792,065 A | 8/1998 | Xue et al. |
| 5,804,047 A | 9/1998 | Karube et al. |
| 5,820,551 A | 10/1998 | Hills et al. |
| 5,822,715 A | 10/1998 | Worthington et al. |
| 5,891,047 A | 4/1999 | Lander et al. |
| 5,891,049 A | 4/1999 | Cyrus et al. |
| 5,899,855 A | 5/1999 | Brown |
| 5,914,026 A | 6/1999 | Blubaugh, Jr. et al. |
| 5,918,603 A | 7/1999 | Brown |
| 5,925,021 A | 7/1999 | Castellano et al. |
| 5,935,224 A | 8/1999 | Svancarek et al. |
| 5,942,979 A | 8/1999 | Luppino |
| 5,951,485 A | 9/1999 | Cyrus et al. |
| 5,957,854 A | 9/1999 | Besson et al. |
| 5,960,797 A | 10/1999 | Kramer et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,972,199 A | 10/1999 | Heller et al. |
| 5,995,860 A | 11/1999 | Sun et al. |
| 6,001,067 A | 12/1999 | Shults et al. |
| 6,016,443 A | 1/2000 | Ekwall et al. |
| 6,021,350 A | 2/2000 | Mathson |
| 6,024,699 A | 2/2000 | Surwit et al. |
| 6,038,469 A | 3/2000 | Karlsson et al. |
| 6,049,727 A | 4/2000 | Crothall |
| 6,071,391 A | 6/2000 | Gotoh et al. |

(56) References Cited

U.S. PATENT DOCUMENTS

| | | |
|---|---|---|
| 6,073,031 A | 6/2000 | Helstab et al. |
| 6,083,710 A | 7/2000 | Heller et al. |
| 6,088,608 A | 7/2000 | Schulman et al. |
| 6,091,976 A | 7/2000 | Pfeiffer et al. |
| 6,091,987 A | 7/2000 | Thompson |
| 6,093,172 A | 7/2000 | Funderburk et al. |
| 6,103,033 A | 8/2000 | Say et al. |
| 6,108,577 A | 8/2000 | Benser |
| 6,112,116 A | 8/2000 | Fischell |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,128,526 A | 10/2000 | Stadler et al. |
| 6,130,623 A | 10/2000 | MacLellan et al. |
| 6,134,461 A | 10/2000 | Say et al. |
| 6,115,628 A | 11/2000 | Stadler et al. |
| 6,143,164 A | 11/2000 | Heller et al. |
| 6,144,837 A | 11/2000 | Quy |
| 6,144,871 A | 11/2000 | Saito et al. |
| 6,159,147 A | 12/2000 | Lichter et al. |
| 6,161,095 A | 12/2000 | Brown |
| 6,162,611 A | 12/2000 | Heller et al. |
| 6,175,752 B1 | 1/2001 | Say et al. |
| 6,200,265 B1 | 3/2001 | Walsh et al. |
| 6,212,416 B1 | 4/2001 | Ward et al. |
| 6,219,574 B1 | 4/2001 | Cormier et al. |
| 6,233,471 B1 | 5/2001 | Berner et al. |
| 6,233,486 B1 | 5/2001 | Ekwall et al. |
| 6,248,067 B1 | 6/2001 | Causey, III et al. |
| 6,249,705 B1 | 6/2001 | Snell |
| 6,254,586 B1 | 7/2001 | Mann et al. |
| 6,256,538 B1 | 7/2001 | Ekwall |
| 6,264,606 B1 | 7/2001 | Ekwall et al. |
| 6,270,455 B1 | 8/2001 | Brown |
| 6,272,379 B1 | 8/2001 | Fischell et al. |
| 6,275,717 B1 | 8/2001 | Gross et al. |
| 6,283,761 B1 | 9/2001 | Joao |
| 6,284,478 B1 | 9/2001 | Heller et al. |
| 6,291,200 B1 | 9/2001 | LeJeune et al. |
| 6,293,925 B1 | 9/2001 | Safabash et al. |
| 6,294,997 B1 | 9/2001 | Paratore et al. |
| 6,295,506 B1 | 9/2001 | Heinonen et al. |
| 6,299,757 B1 | 10/2001 | Feldman et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,338,790 B1 | 1/2002 | Feldman et al. |
| 6,348,640 B1 | 2/2002 | Navot et al. |
| 6,359,444 B1 | 3/2002 | Grimes |
| 6,360,888 B1 | 3/2002 | McIvor et al. |
| 6,361,503 B1 | 3/2002 | Starobin et al. |
| 6,366,794 B1 | 4/2002 | Moussy et al. |
| 6,377,828 B1 | 4/2002 | Chaiken et al. |
| 6,377,852 B1 | 4/2002 | Bornzin et al. |
| 6,377,894 B1 | 4/2002 | Deweese et al. |
| 6,379,301 B1 | 4/2002 | Worthington et al. |
| 6,381,493 B1 | 4/2002 | Stadler et al. |
| 6,387,048 B1 | 5/2002 | Schulman et al. |
| 6,400,974 B1 | 6/2002 | Lesho |
| 6,405,066 B1 | 6/2002 | Essenpreis et al. |
| 6,413,393 B1 | 7/2002 | Van Antwerp et al. |
| 6,416,471 B1 | 7/2002 | Kumar et al. |
| 6,418,346 B1 | 7/2002 | Nelson et al. |
| 6,424,847 B1 | 7/2002 | Mastrototaro et al. |
| 6,427,088 B1 | 7/2002 | Bowman, IV et al. |
| 6,440,068 B1 | 8/2002 | Brown et al. |
| 6,461,496 B1 | 10/2002 | Feldman et al. |
| 6,471,689 B1 | 10/2002 | Joseph et al. |
| 6,478,736 B1 | 11/2002 | Mault |
| 6,484,046 B1 | 11/2002 | Say et al. |
| 6,496,729 B2 | 12/2002 | Thompson |
| 6,497,655 B1 | 12/2002 | Linberg et al. |
| 6,501,983 B1 | 12/2002 | Natarajan et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,520,326 B2 | 2/2003 | McIvor et al. |
| 6,540,891 B1 | 4/2003 | Stewart et al. |
| 6,544,212 B2 | 4/2003 | Galley et al. |
| 6,549,796 B2 | 4/2003 | Sohrab |
| 6,551,494 B1 | 4/2003 | Heller et al. |
| 6,558,320 B1 | 5/2003 | Causey, III et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,975 B1 | 5/2003 | Pool et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,542 B1 | 6/2003 | Houben et al. |
| 6,574,490 B2 | 6/2003 | Abbink et al. |
| 6,574,510 B2 | 6/2003 | Von Arx et al. |
| 6,576,101 B1 | 6/2003 | Heller et al. |
| 6,577,899 B2 | 6/2003 | Lebel et al. |
| 6,579,231 B1 | 6/2003 | Phipps |
| 6,579,690 B1 | 6/2003 | Bonnecaze et al. |
| 6,585,644 B2 | 7/2003 | Lebel et al. |
| 6,591,125 B1 | 7/2003 | Buse et al. |
| 6,592,745 B1 | 7/2003 | Feldman et al. |
| 6,595,919 B2 | 7/2003 | Berner et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,616,819 B1 | 9/2003 | Liamos et al. |
| 6,618,934 B1 | 9/2003 | Feldman et al. |
| 6,622,045 B2 | 9/2003 | Snell et al. |
| 6,633,772 B2 | 10/2003 | Ford et al. |
| 6,635,014 B2 | 10/2003 | Starkweather et al. |
| 6,635,167 B1 | 10/2003 | Batman et al. |
| 6,641,533 B2 | 11/2003 | Causey, III et al. |
| 6,648,821 B2 | 11/2003 | Lebel et al. |
| 6,650,471 B2 | 11/2003 | Doi |
| 6,654,625 B1 | 11/2003 | Say et al. |
| 6,656,114 B1 | 12/2003 | Poulson et al. |
| 6,658,396 B1 | 12/2003 | Tang et al. |
| 6,659,948 B2 | 12/2003 | Lebel et al. |
| 6,668,196 B1 | 12/2003 | Villegas et al. |
| 6,675,030 B2 | 1/2004 | Ciurczak et al. |
| 6,676,816 B2 | 1/2004 | Mao et al. |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,698,269 B2 | 3/2004 | Baber et al. |
| 6,702,857 B2 | 3/2004 | Brauker et al. |
| 6,730,200 B1 | 5/2004 | Stewart et al. |
| 6,731,976 B2 | 5/2004 | Penn et al. |
| 6,731,985 B2 | 5/2004 | Poore et al. |
| 6,733,446 B2 | 5/2004 | Lebel et al. |
| 6,735,183 B2 | 5/2004 | O'Toole et al. |
| 6,736,957 B1 | 5/2004 | Forrow et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,749,740 B2 | 6/2004 | Liamos et al. |
| 6,758,810 B2 | 7/2004 | Lebel et al. |
| 6,764,581 B1 | 7/2004 | Forrow et al. |
| 6,770,030 B1 | 8/2004 | Schaupp et al. |
| 6,773,671 B1 | 8/2004 | Lewis et al. |
| 6,790,178 B1 | 9/2004 | Mault et al. |
| 6,804,558 B2 | 10/2004 | Haller et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,850,790 B2 | 2/2005 | Berner et al. |

(56) References Cited

U.S. PATENT DOCUMENTS

| | | |
|---|---|---|
| 6,862,465 B2 | 3/2005 | Shults et al. |
| 6,865,407 B2 | 3/2005 | Kimball et al. |
| 6,873,268 B2 | 3/2005 | Lebel et al. |
| 6,878,112 B2 | 4/2005 | Linberg et al. |
| 6,881,551 B2 | 4/2005 | Heller et al. |
| 6,882,940 B2 | 4/2005 | Potts et al. |
| 6,892,085 B2 | 5/2005 | McIvor et al. |
| 6,893,545 B2 | 5/2005 | Gotoh et al. |
| 6,895,263 B2 | 5/2005 | Shin et al. |
| 6,895,265 B2 | 5/2005 | Silver |
| 6,923,763 B1 | 8/2005 | Kovatchev et al. |
| 6,923,764 B2 | 8/2005 | Aceti et al. |
| 6,931,327 B2 | 8/2005 | Goode, Jr. et al. |
| 6,932,892 B2 | 8/2005 | Chen et al. |
| 6,932,894 B2 | 8/2005 | Mao et al. |
| 6,936,006 B2 | 8/2005 | Sabra |
| 6,940,403 B2 | 9/2005 | Kail, IV |
| 6,941,163 B2 | 9/2005 | Ford et al. |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,009,511 B2 | 3/2006 | Mazar et al. |
| 7,010,345 B2 | 3/2006 | Hill et al. |
| 7,016,713 B2 | 3/2006 | Gardner et al. |
| 7,016,720 B2 | 3/2006 | Kroll |
| 7,020,508 B2 | 3/2006 | Stivoric et al. |
| 7,022,072 B2 | 4/2006 | Fox et al. |
| 7,022,219 B2 | 4/2006 | Mansouri et al. |
| 7,024,236 B2 | 4/2006 | Ford et al. |
| 7,024,245 B2 | 4/2006 | Lebel et al. |
| 7,025,425 B2 | 4/2006 | Kovatchev et al. |
| 7,029,443 B2 | 4/2006 | Kroll |
| 7,029,444 B2 | 4/2006 | Shin et al. |
| 7,041,068 B2 | 5/2006 | Freeman et al. |
| 7,041,468 B2 | 5/2006 | Drucker et al. |
| 7,043,287 B1 | 5/2006 | Khalil et al. |
| 7,043,305 B2 | 5/2006 | KenKnight et al. |
| 7,052,483 B2 | 5/2006 | Wojcik |
| 7,056,302 B2 | 6/2006 | Douglas |
| 7,058,453 B2 | 6/2006 | Nelson et al. |
| 7,060,031 B2 | 6/2006 | Webb et al. |
| 7,074,307 B2 | 7/2006 | Simpson et al. |
| 7,076,300 B1 | 7/2006 | Kroll et al. |
| 7,081,195 B2 | 7/2006 | Simpson et al. |
| 7,082,334 B2 | 7/2006 | Boute et al. |
| 7,092,891 B2 | 8/2006 | Maus et al. |
| 7,096,064 B2 | 8/2006 | Deno et al. |
| 7,098,803 B2 | 8/2006 | Mann et al. |
| 7,103,412 B1 | 9/2006 | Kroll |
| 7,108,778 B2 | 9/2006 | Simpson et al. |
| 7,110,803 B2 | 9/2006 | Shults et al. |
| 7,113,821 B1 | 9/2006 | Sun et al. |
| 7,118,667 B2 | 10/2006 | Lee |
| 7,123,950 B2 | 10/2006 | Mannheimer |
| 7,125,382 B2 | 10/2006 | Zhou et al. |
| 7,134,999 B2 | 11/2006 | Brauker et al. |
| 7,136,689 B2 | 11/2006 | Shults et al. |
| 7,142,911 B2 | 11/2006 | Boileau et al. |
| 7,153,265 B2 | 12/2006 | Vachon |
| 7,167,818 B2 | 1/2007 | Brown |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,203,549 B2 | 4/2007 | Schommer et al. |
| 7,225,091 B2 | 5/2007 | Tivig et al. |
| 7,225,535 B2 | 6/2007 | Feldman et al. |
| 7,226,978 B2 | 6/2007 | Tapsak et al. |
| 7,228,182 B2 | 6/2007 | Healy et al. |
| 7,237,712 B2 | 7/2007 | DeRocco et al. |
| 7,258,673 B2 | 8/2007 | Racchini et al. |
| 7,267,665 B2 | 9/2007 | Steil et al. |
| 7,272,436 B2 | 9/2007 | Gill et al. |
| 7,276,029 B2 | 10/2007 | Goode, Jr. et al. |
| 7,278,983 B2 | 10/2007 | Ireland et al. |
| 7,295,867 B2 | 11/2007 | Berner et al. |
| 7,297,114 B2 | 11/2007 | Gill et al. |
| 7,299,082 B2 | 11/2007 | Feldman et al. |
| 7,310,544 B2 | 12/2007 | Brister et al. |
| 7,317,938 B2 | 1/2008 | Goode, Jr. et al. |
| 7,335,294 B2 | 2/2008 | Heller et al. |
| 7,354,420 B2 | 4/2008 | Steil et al. |
| 7,364,592 B2 | 4/2008 | Carr-Brendel et al. |
| 7,366,556 B2 | 4/2008 | Brister et al. |
| 7,347,819 B2 | 5/2008 | Lebel et al. |
| 7,379,765 B2 | 5/2008 | Petisce et al. |
| 7,384,397 B2 | 6/2008 | Zhang et al. |
| 7,387,010 B2 | 6/2008 | Sunshine et al. |
| 7,399,277 B2 | 7/2008 | Saidara et al. |
| 7,402,153 B2 | 7/2008 | Steil et al. |
| 7,404,796 B2 | 7/2008 | Ginsberg |
| 7,419,573 B2 | 9/2008 | Gundel |
| 7,424,318 B2 | 9/2008 | Brister et al. |
| 7,429,255 B2 | 9/2008 | Thompson |
| 7,460,898 B2 | 12/2008 | Brister et al. |
| 7,467,003 B2 | 12/2008 | Brister et al. |
| 7,471,972 B2 | 12/2008 | Rhodes et al. |
| 7,474,992 B2 | 1/2009 | Ariyur |
| 7,492,254 B2 | 2/2009 | Bandy et al. |
| 7,494,465 B2 | 2/2009 | Brister et al. |
| 7,497,827 B2 | 3/2009 | Brister et al. |
| 7,499,002 B2 | 3/2009 | Blasko et al. |
| 7,502,644 B2 | 3/2009 | Gill et al. |
| 7,519,408 B2 | 4/2009 | Rasdal et al. |
| 7,524,287 B2 | 4/2009 | Bharmi |
| 7,547,281 B2 | 6/2009 | Hayes et al. |
| 7,565,197 B2 | 7/2009 | Haubrich et al. |
| 7,569,030 B2 | 8/2009 | Lebel et al. |
| 7,574,266 B2 | 8/2009 | Dudding et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,602,310 B2 | 10/2009 | Mann et al. |
| 7,604,178 B2 | 10/2009 | Stewart |
| 7,613,491 B2 | 11/2009 | Boock et al. |
| 7,615,007 B2 | 11/2009 | Shults et al. |
| 7,618,369 B2 | 11/2009 | Hayter et al. |
| 7,630,748 B2 | 12/2009 | Budiman |
| 7,632,228 B2 | 12/2009 | Brauker et al. |
| 7,635,594 B2 | 12/2009 | Holmes et al. |
| 7,637,868 B2 | 12/2009 | Saint et al. |
| 7,640,048 B2 | 12/2009 | Dobbles et al. |
| 7,659,823 B1 | 2/2010 | Killian et al. |
| 7,668,596 B2 | 2/2010 | Von Arx et al. |
| 7,699,775 B2 | 4/2010 | Desai et al. |
| 7,699,964 B2 | 4/2010 | Feldman et al. |
| 7,736,310 B2 | 6/2010 | Taub et al. |
| 7,741,734 B2 | 6/2010 | Joannopoulos et al. |
| 7,766,829 B2 | 8/2010 | Sloan et al. |
| 7,771,352 B2 | 8/2010 | Shults et al. |
| 7,774,145 B2 | 8/2010 | Bruaker et al. |
| 7,778,680 B2 | 8/2010 | Goode, Jr. et al. |
| 7,779,332 B2 | 8/2010 | Karr et al. |
| 7,782,192 B2 | 8/2010 | Jeckelmann et al. |
| 7,783,333 B2 | 8/2010 | Brister et al. |
| 7,791,467 B2 | 9/2010 | Mazar et al. |
| 7,792,562 B2 | 9/2010 | Shults et al. |
| 7,811,231 B2 | 10/2010 | Jin et al. |
| 7,826,981 B2 | 11/2010 | Goode, Jr. et al. |
| 7,831,310 B2 | 11/2010 | Lebel et al. |
| 7,860,574 B2 | 12/2010 | Von Arx et al. |
| 7,866,026 B1 | 1/2011 | Wang et al. |
| 7,882,611 B2 | 2/2011 | Shah et al. |
| 7,889,069 B2 | 2/2011 | Fifolt et al. |
| 7,899,511 B2 | 3/2011 | Shults et al. |

(56) References Cited

U.S. PATENT DOCUMENTS

| | | |
|---|---|---|
| 7,905,833 B2 | 3/2011 | Brister et al. |
| 7,912,674 B2 | 3/2011 | Killoren Clark et al. |
| 7,914,450 B2 | 3/2011 | Goode, Jr. et al. |
| 7,916,013 B2 | 3/2011 | Stevenson |
| 7,938,797 B2 | 5/2011 | Estes |
| 7,946,985 B2 | 5/2011 | Mastrototaro et al. |
| 7,955,258 B2 | 6/2011 | Goscha et al. |
| 7,970,448 B2 | 6/2011 | Shults et al. |
| 7,974,672 B2 | 7/2011 | Shults et al. |
| 7,999,674 B2 | 8/2011 | Kamen |
| 8,216,138 B1 | 7/2012 | McGarraugh et al. |
| 8,282,549 B2 | 10/2012 | Brauker et al. |
| 2002/0019022 A1 | 2/2002 | Dunn et al. |
| 2002/0068860 A1 | 6/2002 | Clark |
| 2002/0072784 A1 | 6/2002 | Sheppard et al. |
| 2002/0103499 A1 | 8/2002 | Perez et al. |
| 2002/0128594 A1 | 9/2002 | Das et al. |
| 2002/0143266 A1 | 10/2002 | Bock |
| 2002/0169635 A1 | 11/2002 | Shillingburg |
| 2002/0193679 A1 | 12/2002 | Malave et al. |
| 2003/0004403 A1 | 1/2003 | Drinan et al. |
| 2003/0023461 A1 | 1/2003 | Quintanilla et al. |
| 2003/0032867 A1 | 2/2003 | Crothall et al. |
| 2003/0050546 A1 | 3/2003 | Desai et al. |
| 2003/0100821 A1 | 5/2003 | Heller et al. |
| 2003/0168338 A1 | 9/2003 | Gao et al. |
| 2003/0191377 A1 | 10/2003 | Robinson et al. |
| 2003/0199790 A1 | 10/2003 | Boecker et al. |
| 2003/0208113 A1 | 11/2003 | Mault et al. |
| 2003/0212379 A1 | 11/2003 | Bylund et al. |
| 2003/0216630 A1 | 11/2003 | Jersey-Willuhn et al. |
| 2003/0217966 A1 | 11/2003 | Tapsak et al. |
| 2004/0010207 A1 | 1/2004 | Flaherty et al. |
| 2004/0039298 A1 | 2/2004 | Abreu |
| 2004/0054263 A1 | 3/2004 | Moerman et al. |
| 2004/0064068 A1 | 4/2004 | DeNuzzio et al. |
| 2004/0106858 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0138716 A1 | 7/2004 | Kon et al. |
| 2004/0146909 A1 | 7/2004 | Duong et al. |
| 2004/0152622 A1 | 8/2004 | Keith et al. |
| 2004/0167801 A1 | 8/2004 | Say et al. |
| 2004/0171921 A1 | 9/2004 | Say et al. |
| 2004/0172307 A1 | 9/2004 | Gruber |
| 2004/0176672 A1 | 9/2004 | Silver et al. |
| 2004/0186365 A1 | 9/2004 | Jin et al. |
| 2004/0197846 A1 | 10/2004 | Hockersmith et al. |
| 2004/0199056 A1 | 10/2004 | Husemann et al. |
| 2004/0204687 A1 | 10/2004 | Mogensen et al. |
| 2004/0208780 A1 | 10/2004 | Faries, Jr. et al. |
| 2004/0249420 A1 | 12/2004 | Olson et al. |
| 2004/0254433 A1 | 12/2004 | Bandis et al. |
| 2004/0254434 A1 | 12/2004 | Goodnow et al. |
| 2004/0260478 A1 | 12/2004 | Schwamm |
| 2004/0267300 A1 | 12/2004 | Mace |
| 2005/0003470 A1 | 1/2005 | Nelson et al. |
| 2005/0004439 A1 | 1/2005 | Shin et al. |
| 2005/0004494 A1 | 1/2005 | Perez et al. |
| 2005/0010087 A1 | 1/2005 | Banet et al. |
| 2005/0016276 A1 | 1/2005 | Guan et al. |
| 2005/0017864 A1 | 1/2005 | Tsoukalis |
| 2005/0027181 A1 * | 2/2005 | Goode, Jr. ............ A61B 5/0031 600/365 |
| 2005/0031689 A1 | 2/2005 | Shults et al. |
| 2005/0043598 A1 | 2/2005 | Goode, Jr. et al. |
| 2005/0049179 A1 | 3/2005 | Davidson et al. |
| 2005/0070774 A1 | 3/2005 | Addison et al. |
| 2005/0090607 A1 | 4/2005 | Tapsak et al. |
| 2005/0114068 A1 | 5/2005 | Chey et al. |
| 2005/0143635 A1 | 6/2005 | Kamath et al. |
| 2005/0176136 A1 | 8/2005 | Burd et al. |
| 2005/0177398 A1 | 8/2005 | Watanabe et al. |
| 2005/0182306 A1 | 8/2005 | Sloan |
| 2005/0195930 A1 | 9/2005 | Spital et al. |
| 2005/0214892 A1 | 9/2005 | Kovatchev et al. |
| 2005/0245795 A1 | 11/2005 | Goode, Jr. et al. |
| 2005/0245799 A1 | 11/2005 | Brauker et al. |
| 2005/0245839 A1 | 11/2005 | Stivoric et al. |
| 2005/0245904 A1 | 11/2005 | Estes et al. |
| 2005/0277912 A1 | 12/2005 | John |
| 2005/0288725 A1 | 12/2005 | Hettrick et al. |
| 2006/0001538 A1 | 1/2006 | Kraft et al. |
| 2006/0004270 A1 | 1/2006 | Bedard et al. |
| 2006/0010098 A1 | 1/2006 | Goodnow et al. |
| 2006/0015020 A1 | 1/2006 | Neale et al. |
| 2006/0017923 A1 | 1/2006 | Ruchti et al. |
| 2006/0025663 A1 | 2/2006 | Talbot et al. |
| 2006/0029177 A1 | 2/2006 | Cranford, Jr. et al. |
| 2006/0031094 A1 | 2/2006 | Cohen et al. |
| 2006/0058588 A1 | 3/2006 | Zdeblick |
| 2006/0091006 A1 | 5/2006 | Wang et al. |
| 2006/0166629 A1 | 7/2006 | Reggiardo |
| 2006/0173260 A1 | 8/2006 | Gaoni et al. |
| 2006/0189863 A1 | 8/2006 | Peyser et al. |
| 2006/0226985 A1 | 10/2006 | Goodnow et al. |
| 2006/0229512 A1 | 10/2006 | Petisce et al. |
| 2006/0247508 A1 | 11/2006 | Fennell |
| 2006/0247685 A1 | 11/2006 | Bharmi |
| 2006/0247710 A1 | 11/2006 | Goetz et al. |
| 2006/0247985 A1 | 11/2006 | Liamos et al. |
| 2006/0258929 A1 | 11/2006 | Goode et al. |
| 2006/0264785 A1 | 11/2006 | Dring et al. |
| 2006/0272652 A1 | 12/2006 | Stocker et al. |
| 2006/0281985 A1 | 12/2006 | Ward et al. |
| 2006/0287691 A1 | 12/2006 | Drew |
| 2007/0016381 A1 | 1/2007 | Kamath et al. |
| 2007/0027381 A1 | 2/2007 | Stafford |
| 2007/0032706 A1 | 2/2007 | Kamath et al. |
| 2007/0033074 A1 | 2/2007 | Nitzan et al. |
| 2007/0055799 A1 | 3/2007 | Koehler et al. |
| 2007/0056858 A1 | 3/2007 | Chen et al. |
| 2007/0060803 A1 | 3/2007 | Liljeryd et al. |
| 2007/0060814 A1 | 3/2007 | Stafford |
| 2007/0066873 A1 | 3/2007 | Kamath et al. |
| 2007/0068807 A1 | 3/2007 | Feldman et al. |
| 2007/0071681 A1 | 3/2007 | Gadkar et al. |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0078323 A1 | 4/2007 | Reggiardo et al. |
| 2007/0095661 A1 | 5/2007 | Wang et al. |
| 2007/0108048 A1 | 5/2007 | Wang et al. |
| 2007/0118405 A1 | 5/2007 | Campbell et al. |
| 2007/0124002 A1 | 5/2007 | Estes et al. |
| 2007/0149875 A1 | 6/2007 | Ouyang et al. |
| 2007/0168224 A1 | 7/2007 | Letzt et al. |
| 2007/0173706 A1 | 7/2007 | Neinast et al. |
| 2007/0173709 A1 | 7/2007 | Petisce et al. |
| 2007/0173710 A1 | 7/2007 | Petisce et al. |
| 2007/0173761 A1 | 7/2007 | Kanderian et al. |
| 2007/0179349 A1 | 8/2007 | Hoyme et al. |
| 2007/0179352 A1 | 8/2007 | Randlov et al. |
| 2007/0179434 A1 | 8/2007 | Weinert et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0213657 A1 | 9/2007 | Jennewine et al. |
| 2007/0232877 A1 | 10/2007 | He |
| 2007/0232878 A1 | 10/2007 | Kovatchev et al. |
| 2007/0232880 A1 | 10/2007 | Siddiqui et al. |
| 2007/0235331 A1 | 10/2007 | Simpson et al. |
| 2007/0244383 A1 | 10/2007 | Talbot et al. |
| 2007/0249922 A1 | 10/2007 | Peyser et al. |
| 2007/0253021 A1 | 11/2007 | Mehta et al. |
| 2007/0255321 A1 | 11/2007 | Gerber et al. |
| 2007/0255531 A1 | 11/2007 | Drew |
| 2007/0258395 A1 | 11/2007 | Jollota et al. |
| 2007/0270672 A1 | 11/2007 | Hayter |
| 2007/0282299 A1 | 12/2007 | Hellwig |
| 2007/0285238 A1 | 12/2007 | Batra |

(56) References Cited

U.S. PATENT DOCUMENTS

| | | |
|---|---|---|
| 2007/0299617 A1 | 12/2007 | Willis |
| 2008/0009692 A1 | 1/2008 | Stafford |
| 2008/0018433 A1 | 1/2008 | Pitt-Pladdy |
| 2008/0033254 A1 | 2/2008 | Kamath et al. |
| 2008/0039702 A1 | 2/2008 | Hayter et al. |
| 2008/0045824 A1 | 2/2008 | Tapsak et al. |
| 2008/0058625 A1 | 3/2008 | McGarraugh et al. |
| 2008/0064937 A1 | 3/2008 | McGarraugh et al. |
| 2008/0064943 A1 | 3/2008 | Talbot et al. |
| 2008/0071157 A1 | 3/2008 | McGarraugh et al. |
| 2008/0071158 A1 | 3/2008 | McGarraugh et al. |
| 2008/0071328 A1 | 3/2008 | Haubrich et al. |
| 2008/0083617 A1 | 4/2008 | Simpson et al. |
| 2008/0086273 A1 | 4/2008 | Shults et al. |
| 2008/0097289 A1 | 4/2008 | Steil et al. |
| 2008/0119703 A1 | 5/2008 | Brister et al. |
| 2008/0119705 A1 | 5/2008 | Patel et al. |
| 2008/0139910 A1 | 6/2008 | Mastrototaro et al. |
| 2008/0154513 A1 | 6/2008 | Kovatchev et al. |
| 2008/0167572 A1 | 7/2008 | Stivoric et al. |
| 2008/0172205 A1 | 7/2008 | Breton et al. |
| 2008/0177149 A1 | 7/2008 | Weinert et al. |
| 2008/0183060 A1 | 7/2008 | Steil et al. |
| 2008/0188796 A1 | 8/2008 | Steil et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0201325 A1 | 8/2008 | Doniger et al. |
| 2008/0208113 A1 | 8/2008 | Damiano et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0234943 A1 | 9/2008 | Ray et al. |
| 2008/0235469 A1 | 9/2008 | Drew |
| 2008/0242961 A1 | 10/2008 | Brister et al. |
| 2008/0242963 A1 | 10/2008 | Essenpreis et al. |
| 2008/0255434 A1 | 10/2008 | Hayter et al. |
| 2008/0255437 A1 | 10/2008 | Hayter |
| 2008/0255438 A1 | 10/2008 | Saidara et al. |
| 2008/0255808 A1 | 10/2008 | Hayter |
| 2008/0256048 A1 | 10/2008 | Hayter |
| 2008/0262469 A1 | 10/2008 | Brister et al. |
| 2008/0267823 A1 | 10/2008 | Wang et al. |
| 2008/0287761 A1 | 11/2008 | Hayter |
| 2008/0287762 A1 | 11/2008 | Hayter |
| 2008/0287763 A1 | 11/2008 | Hayter |
| 2008/0288180 A1 | 11/2008 | Hayter |
| 2008/0288204 A1 | 11/2008 | Hayter et al. |
| 2008/0300572 A1 | 12/2008 | Rankers et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2008/0312841 A1 | 12/2008 | Hayter |
| 2008/0312842 A1 | 12/2008 | Hayter |
| 2008/0312844 A1 | 12/2008 | Hayter et al. |
| 2008/0312845 A1 | 12/2008 | Hayter et al. |
| 2008/0312859 A1 | 12/2008 | Skyggebjerg et al. |
| 2008/0319279 A1 | 12/2008 | Ramsay et al. |
| 2009/0005665 A1 | 1/2009 | Hayter et al. |
| 2009/0005666 A1 | 1/2009 | Shin et al. |
| 2009/0006034 A1 | 1/2009 | Hayter et al. |
| 2009/0006061 A1 | 1/2009 | Thukral et al. |
| 2009/0006133 A1 | 1/2009 | Weinert et al. |
| 2009/0012376 A1 | 1/2009 | Agus |
| 2009/0018424 A1 | 1/2009 | Kamath et al. |
| 2009/0018425 A1 | 1/2009 | Ouyang et al. |
| 2009/0030294 A1 | 1/2009 | Petisce et al. |
| 2009/0033482 A1 | 2/2009 | Hayter et al. |
| 2009/0036747 A1 | 2/2009 | Hayter et al. |
| 2009/0036760 A1 | 2/2009 | Hayter |
| 2009/0036763 A1 | 2/2009 | Brauker et al. |
| 2009/0043182 A1 | 2/2009 | Brauker et al. |
| 2009/0043525 A1 | 2/2009 | Brauker et al. |
| 2009/0048503 A1 | 2/2009 | Dalal et al. |
| 2009/0054745 A1 | 2/2009 | Jennewine et al. |
| 2009/0055149 A1 | 2/2009 | Hayter et al. |
| 2009/0062633 A1 | 3/2009 | Brauker et al. |
| 2009/0062767 A1 | 3/2009 | VanAntwerp et al. |
| 2009/0063402 A1 | 3/2009 | Hayter |
| 2009/0076356 A1 | 3/2009 | Simpson et al. |
| 2009/0076360 A1 | 3/2009 | Brister et al. |
| 2009/0082693 A1 | 3/2009 | Stafford |
| 2009/0085768 A1 | 4/2009 | Patel et al. |
| 2009/0099436 A1 | 4/2009 | Brister et al. |
| 2009/0105554 A1 | 4/2009 | Stahmann et al. |
| 2009/0105560 A1 | 4/2009 | Solomon |
| 2009/0105570 A1 | 4/2009 | Sloan et al. |
| 2009/0105636 A1 | 4/2009 | Hayter et al. |
| 2009/0112478 A1 | 4/2009 | Mueller, Jr. et al. |
| 2009/0118589 A1 | 5/2009 | Ueshima et al. |
| 2009/0124877 A1 | 5/2009 | Shariati et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Ying et al. |
| 2009/0150186 A1 | 6/2009 | Cohen et al. |
| 2009/0163791 A1 | 6/2009 | Brister et al. |
| 2009/0164190 A1 | 6/2009 | Hayter |
| 2009/0164239 A1 | 6/2009 | Hayter et al. |
| 2009/0164251 A1 | 6/2009 | Hayter |
| 2009/0178459 A1 | 7/2009 | Li et al. |
| 2009/0182217 A1 | 7/2009 | Li et al. |
| 2009/0189738 A1 | 7/2009 | Hermle |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192745 A1 | 7/2009 | Kamath et al. |
| 2009/0192751 A1 | 7/2009 | Kamath et al. |
| 2009/0198118 A1 | 8/2009 | Hayter et al. |
| 2009/0204341 A1 | 8/2009 | Brauker et al. |
| 2009/0216103 A1 | 8/2009 | Brister et al. |
| 2009/0234200 A1 | 9/2009 | Husheer |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0247857 A1 | 10/2009 | Harper et al. |
| 2009/0253973 A1 | 10/2009 | Bashan et al. |
| 2009/0267765 A1 | 10/2009 | Greene et al. |
| 2009/0289796 A1 | 11/2009 | Blumberg |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2010/0057040 A1 | 3/2010 | Hayter |
| 2010/0057041 A1 | 3/2010 | Hayter |
| 2010/0057042 A1 | 3/2010 | Hayter |
| 2010/0057044 A1 | 3/2010 | Hayter |
| 2010/0057057 A1 | 3/2010 | Hayter et al. |
| 2010/0063372 A1 | 3/2010 | Potts et al. |
| 2010/0141656 A1 | 6/2010 | Krieftewirth |
| 2010/0160759 A1 | 6/2010 | Celentano et al. |
| 2010/0168538 A1 | 7/2010 | Keenan et al. |
| 2010/0168546 A1 | 7/2010 | Kamath et al. |
| 2010/0174266 A1 | 7/2010 | Estes |
| 2010/0190435 A1 | 7/2010 | Cook et al. |
| 2010/0280441 A1 | 11/2010 | Willinska et al. |
| 2010/0312176 A1 | 12/2010 | Lauer et al. |
| 2011/0004276 A1 | 1/2011 | Blair et al. |
| 2011/0024043 A1 | 2/2011 | Boock et al. |
| 2011/0024307 A1 | 2/2011 | Simpson et al. |
| 2011/0027127 A1 | 2/2011 | Simpson et al. |
| 2011/0027453 A1 | 2/2011 | Boock et al. |
| 2011/0027458 A1 | 2/2011 | Boock et al. |

(56) References Cited

U.S. PATENT DOCUMENTS

| | | |
|---|---|---|
| 2011/0028815 A1 | 2/2011 | Simpson et al. |
| 2011/0028816 A1 | 2/2011 | Simpson et al. |
| 2011/0077490 A1 | 3/2011 | Simpson et al. |
| 2011/0148905 A1 | 6/2011 | Simmons et al. |
| 2011/0152637 A1 | 6/2011 | Kateraas et al. |
| 2011/0208027 A1 | 8/2011 | Wagner et al. |
| 2011/0208155 A1 | 8/2011 | Palerm et al. |
| 2011/0320130 A1 | 12/2011 | Valdes et al. |
| 2012/0078071 A1 | 3/2012 | Bohm et al. |
| 2012/0108934 A1 | 5/2012 | Valdes et al. |
| 2012/0165626 A1 | 6/2012 | Irina et al. |
| 2012/0165640 A1 | 6/2012 | Galley et al. |
| 2012/0215462 A1 | 8/2012 | Goode et al. |
| 2013/0035575 A1 | 2/2013 | Mayou et al. |

FOREIGN PATENT DOCUMENTS

| | | |
|---|---|---|
| EP | 0320109 | 6/1989 |
| EP | 0390390 | 10/1990 |
| EP | 0396788 | 11/1990 |
| EP | 0286118 | 1/1995 |
| EP | 1677668 | 7/2010 |
| WO | WO-2000/059370 | 10/2000 |
| WO | WO-2001/052935 | 7/2001 |
| WO | WO-2001/054753 | 8/2001 |
| WO | WO-2003/082091 | 10/2003 |
| WO | WO-2007/097754 | 8/2007 |
| WO | WO-2008/143943 | 11/2008 |

OTHER PUBLICATIONS

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Isermann, R., "Supervision, Fault-Detection and Fault-Diagnosis Methods—An Introduction", *Control Engineering Practice*, vol. 5, No. 5, 1997, pp. 639-652.

Isermann, R., et al., "Trends in the Application of Model-Based Fault Detection and Diagnosis of Technical Processes", *Control Engineering Practice*, vol. 5, No. 5, 1997, pp. 709-719.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

(56) References Cited

OTHER PUBLICATIONS

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.
Sternberg, R., et al., "Study and Development of Multilayer Needle-Type Enzyme-Based Glucose Microsensors", *Biosensors*, vol. 4, 1988, pp. 27-40.
Thompson, M., et al., "In Vivo Probes: Problems and Perspectives", *Clinical Biochemistry*, vol. 19, 1986, pp. 255-261.
Turner, A., et al., "Diabetes Mellitus: Biosensors for Research and Management", *Biosensors*, vol. 1, 1985, pp. 85-115.
Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.
Velho, G., et al., "Strategies for Calibrating a Subcutaneous Glucose Sensor", *Biomedica Biochimica Acta*, vol. 48, 1989, pp. 957-964.
Wilson, G. S., et al., "Progress Toward the Development of an Implantable Sensor for Glucose", *Clinical Chemistry*, vol. 38, No. 9, 1992, pp. 1613-1617.

\* cited by examiner

ACCURACY OF CONTINUOUS GLUCOSE SENSORS

CROSS-REFERENCE TO RELATED APPLICATIONS

The present application is a continuation of U.S. non-provisional application Ser. No. 12/065,257 filed Aug. 29, 2008, which claims priority to PCT application no. PCT/US2006/033724 filed Aug. 29, 2006, which claims priority to U.S. provisional application No. 60/713,203 filed Aug. 31, 2005 and U.S. provisional application No. 60/815,191 filed Jun. 20, 2006, the disclosures of all of which are incorporated herein by reference for all purposes.

GOVERNMENT LICENSE RIGHTS

This invention was made with government support under Grant number ROI DK51562 awarded by the National Institutes of Health. The government has certain rights in the invention.

TECHNICAL FIELD OF THE INVENTION

The present invention relates to the art of glucose monitoring, and more particularly to methods and systems for continuous glucose monitoring.

BACKGROUND OF THE INVENTION

Existing evidence, such as "National Diabetes Fact Sheet" by American Diabetes Association, indicates that currently approximately 18.2 million people in the U.S. have diabetes; and diabetes is the sixth-leading cause of death in the U.S. One in three Americans born in the year 2000 will develop Type 2 diabetes. With the large number of diabetes patients, and with the incidence of diabetes expected to increase, there is a continuously growing need for accurate glucose monitoring systems to monitor glucose levels. Continuous glucose sensors are designed to provide not only real-time glucose levels at a single point in time, but also the trend of a person's glucose levels based on analysis taking place every certain period of time with minimal finger-sticks, leading to improved glycemic/diabetes control.

Most contemporary continuous glucose sensors (hereafter CGS), however, yield blood glucose (hereafter BG) estimates by sampling interstitial glucose (hereafter IG) in interstitial fluid, rather than BG due to the difficulty in directly measuring BG in artery or blood vessels. A typical glucose (BG) estimation from IG is produced from at least two consecutive approximation steps: 1) Blood-to-interstitial glucose (BG-to-IG) transport; and 2) Derivation of BG values from IG-related electrical current recorded by the sensor. As a result, although CGS technology has made dramatic strides, the development of accurate and reliable CGS devices continues to face numerous challenges in terms of calibration, sensitivity, stability, and physiological time lag between blood and interstitial glucose concentrations. The difference between BG and CGS readings arises from following major factors: physiology, sensor calibration, noise, and engineering. The physiological time lag and gradients are changing dynamically with time, with BG levels, and across subjects; and the direct frequent in vivo sampling of IG is extremely difficult. Consequently, the evaluation of engineering performance of CGS is left with a central problem: separating the portion of BG/CGS error due to calibration, sensor noise, and BG/IG gradient.

Therefore, a method and apparatus are desired for improving accuracy and reliability of CGS.

SUMMARY OF THE INVENTION

Various objects and advantages of the preferred embodiments of the present invention will be appreciated based on this disclosure. According to the preferred embodiments, the present invention improves the accuracy and reliability of CGS by improving the calibration of CGS sensors or remedying errors due to physiological time lag or a combination thereof.

As an exemplary embodiment of the invention, a method for improving accuracy of a continuous glucose sensor (CGS) is disclosed herein. The method comprises: calibrating the CGS at a first time; and changing the CGS calibration at a second time that is determined based upon a dynamically monitored CGS value, a rate of CGS change, and a predetermined criterion.

As another exemplary embodiment of the invention, a method for improving accuracy of a continuous glucose sensor (CGS) is disclosed herein. The method comprises: calibrating the CGS using a first blood glucose data and a second blood glucose data different from the first glucose data.

As yet another exemplary embodiment of the invention, a continuous glucose sensing (CGS) device is disclosed herein. The device comprises: first means for measuring interstitial glucose level so as to obtain a CGS output; and a calibration module accessible to the CGS output for improving accuracy of the CGS, further comprising: a monitoring module accessible to the CGS output for dynamically monitoring the CGS and a time derivative of the CGS; and instructing another calibration event based on the dynamic CGS value, the time derivative of the CGS value, and a predetermined criterion.

As yet another exemplary embodiment of the invention, a computer-readable medium having computer executable instructions for performing a method for improving accuracy of a continuous glucose sensor is disclosed, wherein the method comprises: retrieving an initial blood glucose value and a CGS value obtained in a measurement for the initial blood glucose value; monitoring the CGS value and a time derivative of the CGS value over time; determining whether to initiate another calibration based on the monitored CGS values and the time derivative of the CGS value; and calibrating the CGS if it is determined to initiate said another calibration.

As yet another exemplary embodiment of the invention, a computer-readable medium having computer executable instructions for performing a method for improving accuracy of a continuous glucose sensor is disclosed, wherein the method comprises: retrieving a blood glucose value and a CGS value obtained in a measurement for the initial blood glucose value at a first time; and calibrating the CGS at a second time determined by a CGS value at substantially the second time, a time derivative of the CGS, and a predetermined criterion.

As yet another exemplary embodiment of the invention, a system used for treating a disease associated with blood glucose is disclosed herein. The system comprises: a continuous glucose device; means for delivering the CGS values to a disease treating center that is capable of issuing a corresponding treating instruction or taking a corresponding treating action.

Various objects and/or advantages of some preferred embodiments of the invention can be, in some preferred examples, achieved via the features of the independent claims attached hereto. Additional preferred embodiments are further set forth in the dependent claims. In the claims, only elements denoted by the words "means for" are intended to be interpreted as means plus function claims under 35 U.S.C. § 112, the sixth paragraph.

BRIEF DESCRIPTION OF THE DRAWINGS

The preferred embodiments of the invention can be best understood from the following detailed description taken in conjunction with the accompanying drawings of which.

DETAILED DESCRIPTION OF EXEMPLARY EMBODIMENTS

This invention provides a method and device for improving accuracy of continuous glucose sensors by improving the calibration of the CGS or by remedying errors arising from the physiological time lag between BG and IG, or a combination thereof. In view of many possible variations within the spirit of the invention, the invention will be discussed in the following with reference to specific examples. However, it will be appreciated by those skilled in the art that the following discussion is for demonstration purposes, and should not be interpreted as a limitation. Other variations without departing from the spirit of the invention are also applicable.

Inaccuracies of most current CGS devices are mainly attributed to poor CGS calibration, physiology time lag, and random errors. To reduce the inaccuracy of the CGS, an improved calibration procedure is proposed. The reduction of inaccuracy can alternatively be achieved by remedying the error related to physiological time lag, which is also proposed in this invention. In fact, the improved calibration procedure and the time lag remedy procedure can alternatively be combined together so as to achieve a better performance of CGS.

Figure 1:
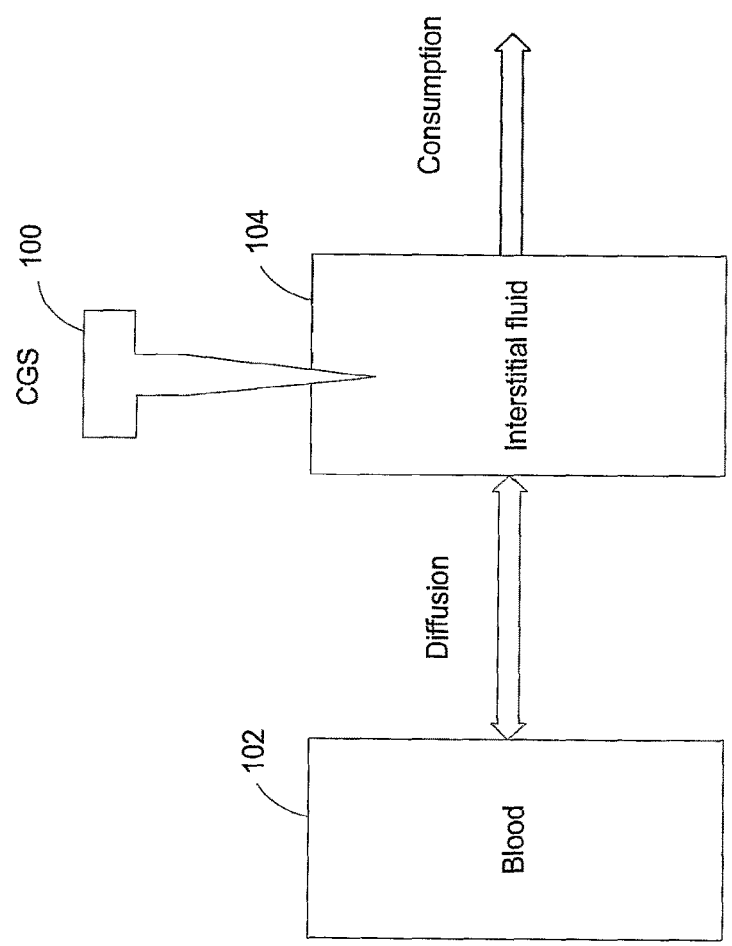
FIG. 1 schematically illustrates a method for measuring blood glucose levels using a continuous glucose sensor according to an example of the invention.

Referring to FIG. 1, a method of measuring glucose levels in vivo according to an example of the invention is schematically illustrated therein. Because of the large difficulty in directly measuring glucose levels in blood vessels or arteries 102, CGS 100 detects blood glucose level by measuring the glucose level in interstitial fluid 104 that interacts with blood vessels or arteries; and associating the output value of the CGS to the blood glucose level (the process is often referred to as calibration). This indirect measurement stands on the proven basis that the blood glucose level co-varies with the glucose level in the interstitial fluid.

Figure 2:
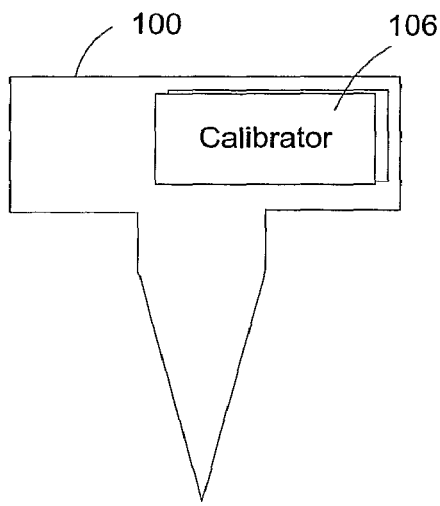
FIG. 2 is an exploded diagram showing the continuous glucose sensor comprising a calibrator of FIG. 1.

To improve the accuracy of CGS, accuracy improver 106 is provided as shown in FIG. 2. The accuracy improver can improve the accuracy of the CGS by improving the CGS calibration through an optimal calibration recommendation (which will be discussed afterwards), or by remedying the error related to the physiology time lag (which will be discussed afterwards), or by a combination thereof. Even though FIG. 2 shows that the accuracy improver is included in the CGS (100) as a functional member, it is not required to be so. In other examples, the accuracy improver can be a stand-alone module or method that is separate from the CGS. Specifically, the accuracy improver can be implemented in a device in connection to the CGS output for improving the accuracy of the CGS. Moreover, the accuracy module can be implemented in the form of a sequence of computer-executable codes stored in a computer-readable medium; or can be implemented in hardware of the device, which will be detailed afterwards.

Figure 3:
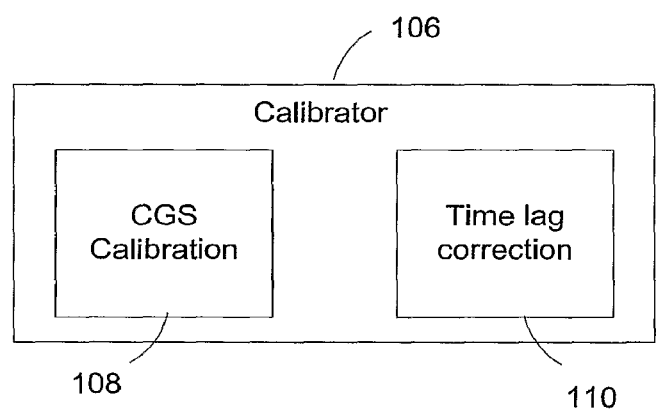
FIG. 3 is a block diagram illustrates functional modules of the calibrator and the time lag corrector according to an example of the invention.

As an example of the invention, FIG. 3 schematically illustrates an exploded view of the accuracy improver (106) in FIG. 2. In this particular example, the accuracy improver (106) comprises CGS calibration module 108 and time lag correction module 110. The CGS calibration module, by performing an optimal calibration recommendation cycle, is designated for improving the calibration of the CGS, thus improving the overall accuracy of the CGS. The time lag correction module (110) is designated for remedying the error from the physiology time lag between the blood glucose and interstitial glucose levels. Depending upon the specific function of the accuracy improver as discussed above, the accuracy improver may have only one or both of the CGS calibration and time lag correction modules.

Improved CGS Calibration

It is known in the art that the accuracy of CGS calibration depends on the rate of blood glucose change and the BG value (BG(t)) at the time (t) of calibration. The rate of BG change can be mathematically expressed as the time derivative of BG(t):d(BG(t))/dt. Given the fact that calibrations with variant inputs are better than those with single or non-varying inputs, the CGS calibration of the invention uses variant inputs.

As an example, FIG. 4 a is a diagram showing functional modules of an exemplary CGS calibration (108) of FIG. 3. Referring to FIG. 4 a, CGS calibrator 108 comprises initial calibration module 111, storing module 113, reassigning module 115, and decision loop module 117 that further comprises monitoring module 119, internal request module 121, self-check initiation module 123, determining module 125, and sensor calibration module 129.

The initial calibration module performs initial calibration so as to obtain an initial calibration data pair SG(0) and BG(0) from an initial measurement of BG(0). Storing module 113 couples to the output of the initial calibration module 111 and stores the initial calibration data pair SG(0) and BG(0). Monitoring module 119 connects to the output of the storing module and dynamically monitors the CGS output SG(t) and the rate of SG(t) change SG'(t)=dSG(t)/dt. Internal request module 121 connects to the output of the monitor module and manages internal requests for calibration. Self-check initiation module 123 is connected to the output of the internal request module and designated for initiating a self-check procedure for optimal calibration timing. In connection with the output of self-check module 123, determining module 125 makes decisions of whether to perform another calibration by sensor calibration module 129 at the particular time. The calibration data from the calibration after the decision are reassigned to the CGS through reassign module 115.

It is noted that one or more above functional modules can be incorporated into other functional modules in practice. In particular, sensor calibration module 129 can be incorporated into initial sensor calibration module 111 for performing CGS calibration. Any of monitor module 119, internal request module 121, self-check module 123, and determining module 125 can be incorporated into combined functional module(s).

Figure 4A:
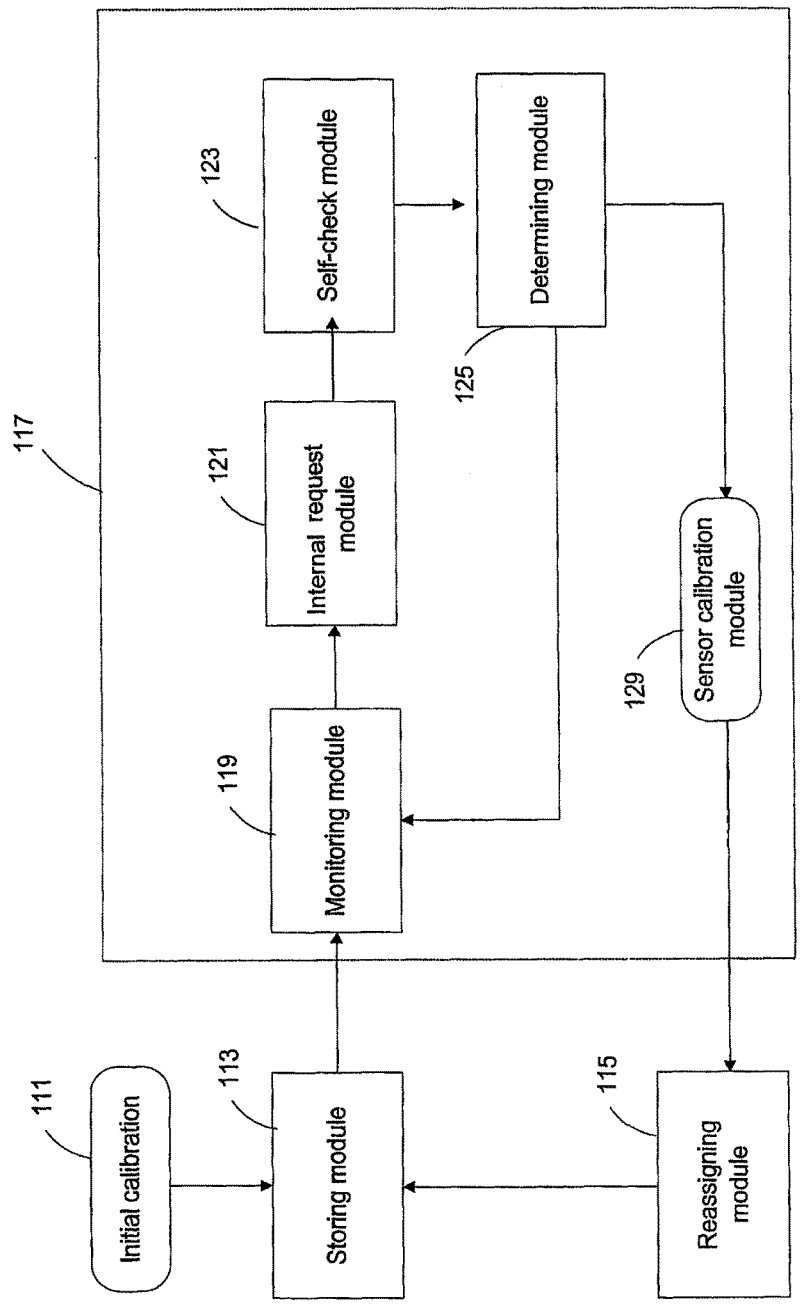
FIG. 4a is a block diagram of the calibration module according to an example of the invention.
Figure 4B:
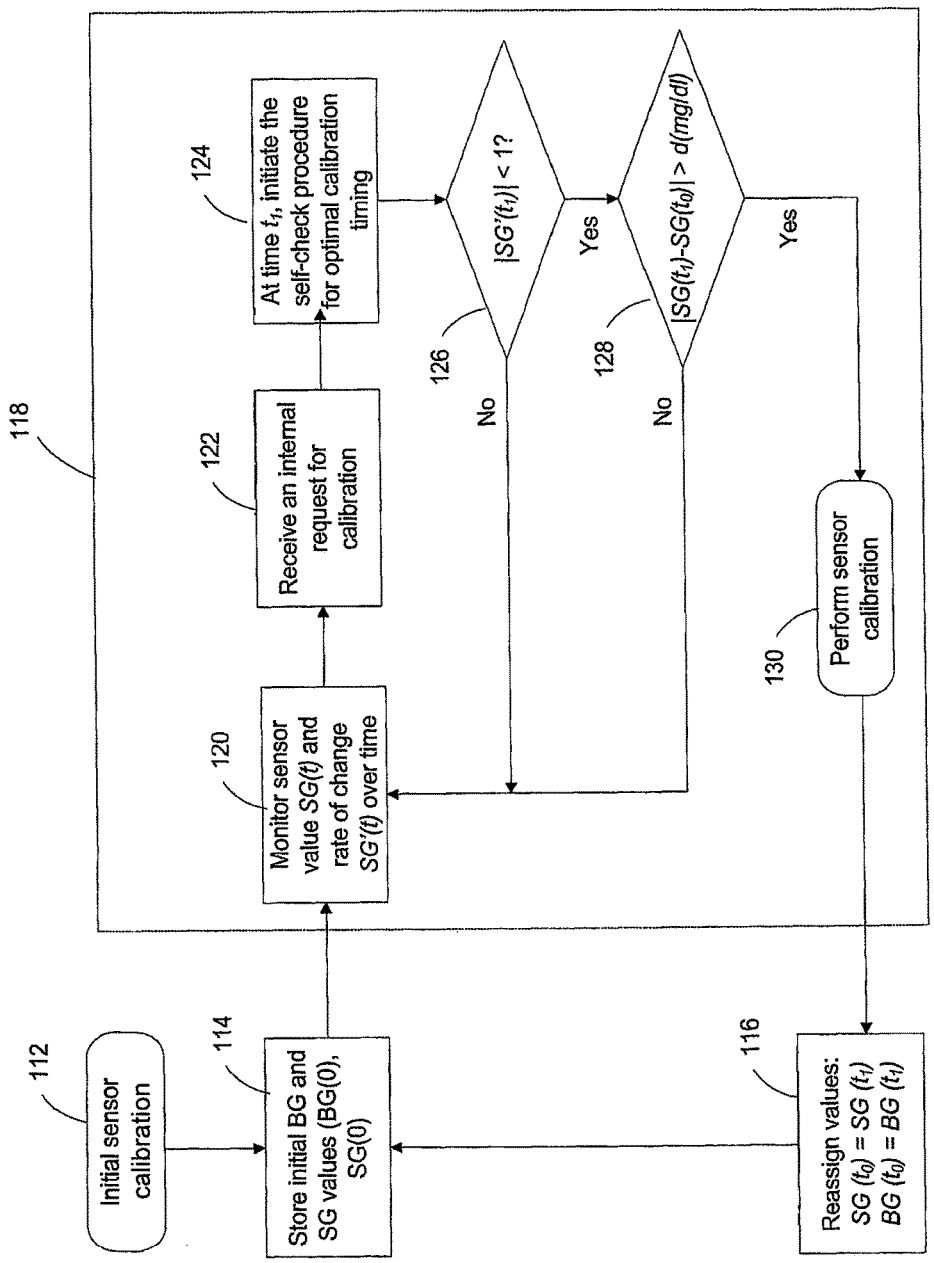
FIG. 4b is a flow chart of a calibration process according to an example of the invention.

An exemplary operation of the functional modules in FIG. 4a, so as to accomplish the desired optimal calibration recommendation process of the invention, is schematically illustrated in FIG. 4b. Referring to FIG. 4b, an initial calibration is performed by measuring the blood glucose level BG(0) at the initial time t so as to obtain an initial CGS output SG(0) (step 112). This step can be performed by initial calibration module 111 in FIG. 4a. The initial pair of data: BG(0) and SG(0) is recorded at step 114. This step can be performed by storing module 113 in FIG. 4a. Such initial calibration can be performed at a time recommended by the CGS manufacturer, or at a time determined by the user. The calibration procedure then enters to calibration decision making loop 118 that is administrated by decision loop module 117 as shown in FIG. 4a.

The calibration decision making loop starts from step 120 that monitors sensor values SG(t) and the rate of change SG'(t) over time with SG'(t) being defined as the first order time derivative of SG(t), that is SG'(t)=dSG(t)/dt. The dynamic monitoring and derivation of the SG'(t) can be performed by monitor module 119 in FIG. 4a. Upon receiving another calibration request at a specific time t1 (step 122), a self-check procedure for optimal calibration timing is initiated at step 124. This step triggers the sequence of actions determining whether a calibration should be performed or not performed at this time, e.g. 126 and 128 in FIG. 4b. The receiving of the calibration request and delivering such request to initiate the self-check procedure can be accomplished by the internal request module 121 in FIG. 4a; and the self-check initiation can be accomplished by the self-check initiation module 123 in FIG. 4a. It is noted that the internal request for another calibration can be initiated at the time defined by the manufacturer, or alternatively, by a time defined by the user, such as a doctor or even proper patients.

Following the initiation of the self-check procedure at step 124, it is determined whether $|SG'(t_1)|<1$ mg/dl/time at step 126. This determination step can be performed by determination module 125 in FIG. 4a. If $|SG(t_1)|\geq 1$ mg/dl/time, the procedure flows back to step 120 to continuously monitoring the SG(t) and SG'(t) values. Otherwise, the procedure makes another determination of whether $|Sg(t_1)-SG(t_o)|$ is greater than d(mg/dl), wherein d(mg/dl) is the pre-determined difference threshold between the initial SG(0) and the CGS output at time $t_1$ $SG(t_1)$. As an example, d(mg/dl) can be 10 mg/dl or higher, such as 15 mg/dl or higher, and more preferably 30 mg/dl or higher. Either one or both of the determinations at steps 126 and 128 can be performed by determination module 125 as shown in FIG. 4a. If $|Sg(t_1)-SG(t_o)|$ is equal to or less than d(mg/dl) at step 128, the procedure flows back to step 120. Otherwise, another calibration is performed at step 130, by for example, sensor calibration module 129 in FIG. 4a. The CGS calibration values are reassigned at step 116 based on the recalibration at step 130, for example, by respectively replacing the calibration values $SG(t_o)$ and $BG(t_o)$ with the recalibrated values $SG(t_1)$ and $BG(t_1)$. The reassigned calibration values are stored at step 114. The above reassignment can be accomplished by reassigning module 115 in FIG. 4a.

After reassigning and recording, the calibration process re-enters the decision making cycle 118, and repeat the above steps 114, 120, 122, 124, 126, 128, 130, and 116. The number of calibration cycles can be determined by the default number of calibrations suggested by the CGS manufacturer, or alternatively, by the user. As an example, a plurality of calibration cycles—e.g. 2 to 10, or more typically 3 to 4 calibration cycles can be performed during the first 24 hours of CGS life.

Figure 5:
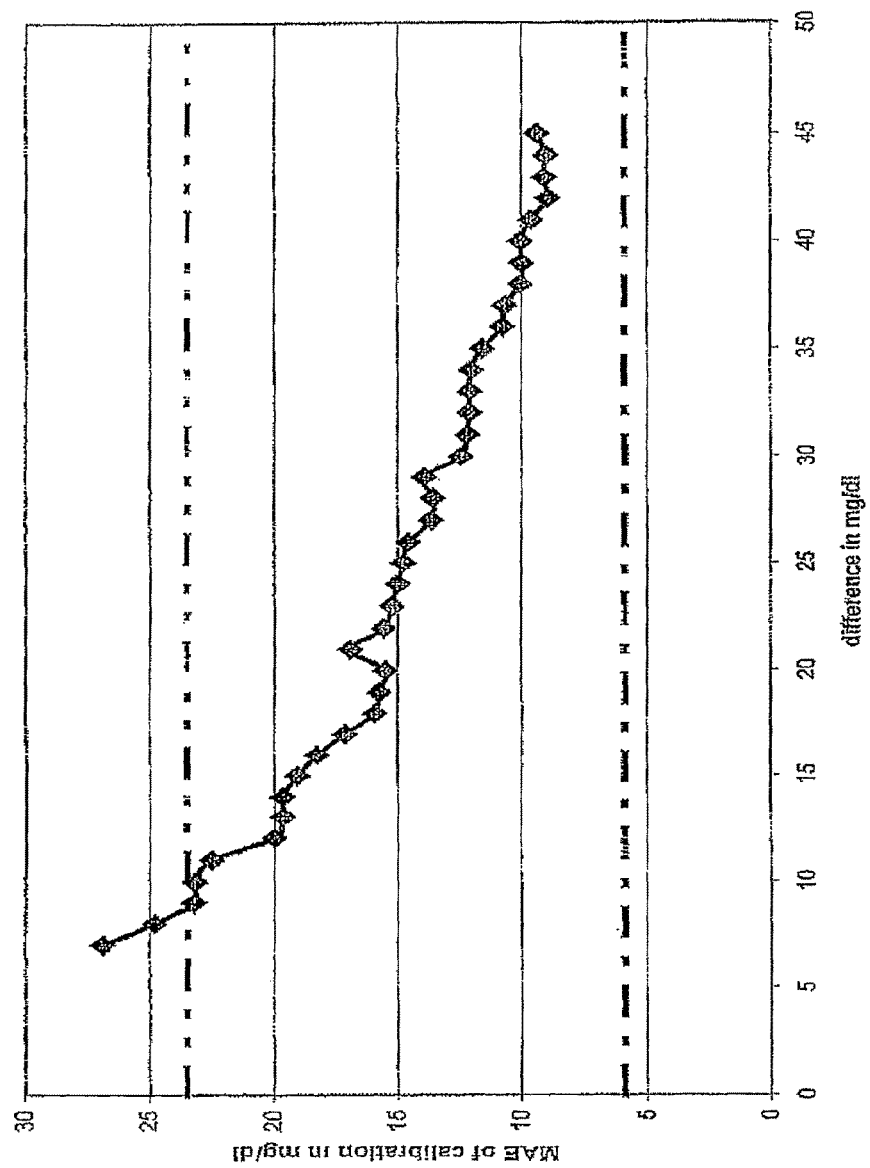
FIG. 5 illustrates therein the blood glucose differential during calibration and the accuracy of the CGS improved by an exemplary method of the invention.

The improved accuracy of CGS using the optimal calibration method as discussed above can be validated by the following experimental data and computer-simulations, as shown in FIG. 5.

Experimental Data

To test the accuracy of the CGS incorporating the accuracy improvement method as discussed above, a measurement is conducted on thirty-nine (39) subjects with type 1 diabetes mellitus (T1DM). The 39 participants have the following statistics: average age 42.5 years with standard deviation (SD) of 12 (SD=12), average duration of T1DM 21.6 years (SD=94), average HbA1c=7.4% (SD=0.8), 16 males.

The study was approved by the University of Virginia IRB Subjects. The subjects were admitted to the general clinic research center (GCRC) in the evening prior to the study. The participants' BG levels were controlled overnight within euglycemic range of 100-150 mg/dl (55-8.3 mmol/l). A Minimed CGMS™ was attached to each subject and was calibrated during the study in accordance with the manufacturer's instructions. All CGMS™ were inserted in the abdomen. Hyperinsulmemic clamps were performed in the morning. Each clamp used constant insulin infusion rate of 1 mU/kg/min and variable glucose infusion rate to achieve and maintain BG levels at approximately 110 mg/dl (around 6 mmol/l). Subsequently, the glucose infusion rate was reduced to permit a controlled decline in BG of approximately 1 mg/dl/min until BG reached 50 mg/dl (around 2.8 mmol/l). Glucose infusion was then resumed to allow a recovery to normal glucose levels. The euglycemic portion of the clamp study varied in length from 70 to 210 minutes; and the duration of the BG reduction procedure ranged from 30 to 60 minutes. The recovery ranged from 30 to 60 minutes. Arterialized blood was achieved by warming the hand to 50° C. and was sampled every 5 minutes for reference BG levels. To allow for insulin to reach its steady state effect, the first 15 minutes of data after the beginning of infusion were ignored. CGMS™ readings were synchronized with reference BG.

Computer Simulation of Sensor Optimal Calibration

A recalibration of the sensor using 2 reference BG values taken during the clamp study described above is computer-simulated, as shown in FIG. 5 that presents the sensor error as a function of the difference between the two BG values. The simulated recalibration uses the standard linear calibration function of the CGMS™. The results from the recalibration are compared to the sensors' own accuracy displayed during the experiment and to a "perfect" calibration using all available reference BG values.

Referring to FIG. 5, the X-axis presents the distance between two simulated calibration points in BG units (mg/dl); and the Y-axis presents the mean absolute error (MAE) of the sensor output with the two-point calibration. It can be seen in the figure that MAE is high if the two calibration BGs are close by value. MAE decreases rapidly when the difference approaches 20 mg/dl, and slowly decreases thereafter. The upper horizontal line in the figure represents the MAE of the sensor's own calibration; and the lower horizontal line represents the MAE resulting from a "perfect" calibration using all available reference points.

It can also be seen in the figure that the BG calibration difference d with value larger than 30 mg/dl but lower than 40 mg/dl achieves excellent results; whereas the difference d with a value larger than 40 mg/dl achieves "nearly-perfect" results. It is worthwhile to point that the sensor calibration during the experiment described above was always done in periods of steady BG kept at euglycemia, thus the influence of BG rate of change was minimal.

Correction of Physiology Time Lag

In addition to the calibration of CGS, physiology time lag between BG and IG also causes inaccuracy in the CGS output. This arises from the fact that most of current CGS devices do not directly measure the blood glucose levels, but the IG levels in the interstitial fluids instead. CGS devices then convert the IG readings into estimates of BG. Therefore, an improved conversion method from IG to BG will lead to improved performance of CGS. An object of the invention improves the conversion from IG to BG by including the physiology time lag between the IG and BG levels. Such improvement is accomplished through analyses and incorporation of the time dependency between IG and BG. Specifically, a mathematical model is established for describing the time dependency among BG and IG or CGS output. Based upon the established model, a mathematical equation is derived to quantitatively express the time dependence of CGS output on BG—that is CGS is a function of BG. This equation is then converted so as to express BG as a function of CGS. The inverted equation can thus be used to predict the BG level for given CGS output values. In application, the inverted equation is applied to the raw CGS data to produce accurate BG estimates.

Mathematical Model

Given the fact that glucose is a relatively small molecule, it is believed that glucose can diffuse freely through capillary wall, such as blood vessels and adipose tissues. Adipose tissue is highly vascularized; and the interstitial fluid occupies a relatively thin layer between cells. This fact implies that there is no volume element that is very far from a cell surface, nor is it very far from a capillary wall. Therefore, uptake and diffusion of glucose in the interstitial fluid can be assumed to be relatively topologically uniform.

The transportation behavior of the IG and BG according to the invention is depicted in FIG. 1. Referring again to FIG. 1, the transport behavior of glucose between interstitial fluid and blood vessels (or adipose tissues) can be modeled as diffusion. IG in the interstitial fluid also experiences consumption, which results in amount and/or concentration reduction.

For deriving a mathematical diffusion equation, it is assumed that the particular local interstitial environment in question does not significantly contribute to the development of the BG/time curve, therefore, the time dependence of BG level, BG(t), evolves independently, and can be treated as an exogenous variable in the system. This assumption is particularly safe especially in hyperinsulinemic clamp situations where the BG level is mostly controlled by the IV infusion of dextrose. It is further assumed that the uptake of glucose follows either an IG independent path, or one described by Michaelis-Menten kinetics, as expressed respectively in equations 1a and 1b:

$$\overset{*}{IG}(t)\Big|_{UU} = \frac{dIG(t)}{dt_{UU}} = -\alpha(t) \qquad \text{Eq. 1a}$$

$$\overset{*}{IG}(t)\Big|_{MM} = \frac{dIG(t)}{dt_{MM}} = -\alpha(t)\frac{IG(t)}{Km + IG(t)} \qquad \text{Eq. 1b}$$

In the above equations, α is the uptake of glucose per unit time per unit volume.

It is noted that equations 1a and 1b describe the explicit time dependence. Other variables, such as insulin levels, exercise, and the like, which may directly affect the glucose uptake BG and IG, are not excluded from the equations. Km is a constant in equation 1b; and it does not introduce additional fittable parameters. In practice, Km can take those published values for the activity of GLUI-4, as set forth in "*Whole body glucose metabolism*" by Zierler K, in *Am J Physiol.* 276:E409-E426, 1999, the subject matter of which is incorporated herein by reference in its entirety. By referring to Fick's Law, the change in IG(t) due to diffusion from the blood can be described by equation 2:

$$\overset{*}{IG}(t)\Big|_{diffusion} = \beta \times [BG(t) - IG(t)] \qquad \text{Eq. 2}$$

where β is the permeability of the capillary wall to glucose. Since there are no other clear sources or sinks of glucose in the interstitial fluid, the net change of glucose can be derived by adding equations 1a and 1b, which can be expressed as the following equations 3a and 3b, wherein equation 3a corresponds to the uniform uptake diffusion model, and equation 3b corresponds to the Michaelis-Menten kinetic model.

$$\overset{*}{IG}(t)\Big|_{net-UU} = \frac{dIG(t)}{dt_{net-UU}} = \beta \times [BG(t) - IG(t)] - \alpha(t) \qquad \text{Eq. 3a}$$

$$\overset{*}{IG}(t)\Big|_{net-MM} = \frac{dIG(t)}{dt_{net-MM}} = \beta \times [BG(t) - IG(t)] - \alpha(t)\frac{IG(t)}{Km + IG(t)} \qquad \text{Eq. 3b}$$

Mathematical Solutions for Equations 3a and 3b

Equation 3a is an ordinary differential equation that has analytical solutions; while equation 3b is a non-linear differential equation of the second type Abel equation that requires numerical simulation. The analytical solution for equation 3a is expressed in the following equation 4:

$$IG(t)|_{net-UU} = e^{-\beta t} \times [\int_0^t [\beta \times BG(s) - \alpha \times IG(ts)]e^{st}ds] \qquad \text{Eq. 4}$$

By assuming that α and β are constant over time, equation 4 can be reduced to the following equation 6 using the Delta-tau notation as presented in the following equation 5:

$$\Delta^\tau(f(t)) \equiv f(t) - e^{-\beta(t-\tau)} f(\tau) \quad \text{Eq. 5}$$

$$IG(t) = IG(\tau)e^{-\beta(t-\tau)} + \sum_{I=0}^{\infty} \left(\frac{-1}{\beta}\right)^i \Delta^\tau(BG^i - \alpha/\beta) \quad \text{Eq. 6}$$

By removing the higher order derivative terms of BG(t) in equation 6, equation 6 can then be reduced to a form to which a Kalman recursion analysis based on Kalman filtering/smoothing technique are applicable. An exemplary of such technique is set forth in "Optimal Control and Estimation" New York: Dover Publications, 1994 37, the subject matter of which is incorporated herein by reference in entirety, wherein a "state-space model" and recursion process are used. The recursion process is attached herein in Appendix B. Using the "state-space model" and with the assumption that CGS readings are uniformly spaced by a small time, $\xi$ a state-space model for dependence of CGS output and IG can be described in the following equation 9.

$$CGS(t_i) = \text{calibration} \times IG(t_i) + R \times w_0, \quad \text{Eq. 9}$$

wherein $IG(t_i) = e^{-\beta\tau} \times IG(t_{i-\xi}) + f(t_i) + Q \times w_s$;

and wherein $f(t_i) = \sum_{j=0}^{\infty} \left(\frac{-1}{\beta}\right)^j \Delta^\tau(BG(t)^j - \alpha/\beta)$.

A state-space model for CGS output including the BG evolution can be expressed as the following equation 10.

$$\begin{bmatrix} BG_{i+1} \\ \overset{*}{BG}_{i+1} \\ \overset{**}{BG}_{i+1} \\ BG_i \\ \overset{*}{BG}_i \\ \overset{**}{BG}_i \\ IG_i \\ \alpha \end{bmatrix} = \begin{bmatrix} 1 & \varepsilon & 0 & 0 & 0 & 0 & 0 & 0 \\ 0 & 1 & \varepsilon & 0 & 0 & 0 & 0 & 0 \\ 0 & 0 & 1 & 0 & 0 & 0 & 0 & 0 \\ 1 & 0 & 0 & 0 & 0 & 0 & 0 & 0 \\ 0 & 1 & 0 & 0 & 0 & 0 & 0 & 0 \\ 0 & 0 & 1 & 0 & 0 & 0 & 0 & 0 \\ 1 & -\frac{1}{\beta} & \frac{1}{\beta^2} & -e^{-\beta\varepsilon} & \frac{e^{-\beta\varepsilon}}{\beta} & \frac{e^{-\beta\varepsilon}}{\beta^2} & e^{-\beta\varepsilon} & -\frac{1}{\beta} \\ 0 & 0 & 0 & 0 & 0 & 0 & 0 & 1 \end{bmatrix} \times \quad \text{Equation 10}$$

$$\begin{bmatrix} BG_i \\ \overset{*}{BG}_i \\ \overset{**}{BG}_i \\ BG_{i-1} \\ \overset{*}{BG}_{i-1} \\ \overset{**}{BG}_{i-1} \\ IG_{i-1} \\ \alpha \end{bmatrix} + Q \times w_s \begin{vmatrix} 0 \\ 0 \\ \varepsilon \\ 0 \\ * \\ 0 \\ 0 \\ 0 \end{vmatrix}$$

A state-space model for CGS output including the BG evolution and linear projection can be expressed as the following equation 11.

$$\begin{bmatrix} BG_{i+1} \\ \overset{*}{BG}_{i+1} \\ \overset{**}{BG}_{i+1} \\ IG_{i+1} \\ \alpha \end{bmatrix} = \begin{bmatrix} 1 & \varepsilon & 0 & 0 & 0 \\ 0 & 1 & \varepsilon & 0 & 0 \\ 0 & 0 & 1 & 0 & 0 \\ \beta\varepsilon & 0 & 0 & 1-\beta\varepsilon & -\varepsilon \\ 0 & 0 & 0 & 0 & 1 \end{bmatrix} \times \begin{bmatrix} BG_i \\ \overset{*}{BG}_i \\ \overset{**}{BG}_i \\ IG_i \\ \alpha \end{bmatrix} + Q \times w_s \begin{bmatrix} 0 \\ 0 \\ \varepsilon \\ 0 \\ 0 \end{bmatrix} \quad \text{Eq. 11}$$

Inversion of equations 3a and 3b can be similarly performed given the estimates of consumption, permeability, IG, and the rate of change of IG. The inversed equations of 3a and 3b are respectively presented as the following equations 12a and 12b:

$$BG(t) = \frac{\overset{*}{IG}(t) + \alpha(t)}{\beta} + IG(t) \quad \text{Eq. 12a}$$

$$BG(t) = \frac{\overset{*}{IG}(t)}{\beta} + IG(t) \times \left[1 + \frac{\alpha/\beta}{Km + IG(t)}\right] \quad \text{Eq. 12b}$$

Equations 12a and 12b indicate that the use of CGS becomes important to provide accurate estimates of the rate of change of IG. Presentations of the inversed equations 12a and 12b are also possible, which are expressed as following equations 13 and 14.

$$\begin{bmatrix} IG(t_i) \\ IG(t_{i-1}) \\ CGS(t_{i+1}) \end{bmatrix} = \begin{bmatrix} 0 & 0 & \text{calib} \\ 1 & 0 & 0 \\ 0 & 0 & 0 \end{bmatrix} \times \begin{bmatrix} IG(t_{i-1}) \\ IG(t_{i-2}) \\ CGS(t_i) \end{bmatrix} + \quad \text{Eq. 13}$$

$$\begin{bmatrix} 0 \\ 0 \\ CGS(t_{i+1}) \end{bmatrix} + Q \times w_s \begin{bmatrix} 1 \\ 0 \\ 0 \end{bmatrix}$$

$$f(t_i) = [1 \quad -e^{-\beta\varepsilon} \quad 0] \times \begin{bmatrix} IG(t_i) \\ IG(t_{i-1}) \\ CGS(t_{i+1}) \end{bmatrix} + R \times w_0 \quad \text{Eq. 14}$$

It is noted that the observation in the above described model is the function of BG(t) that defined in equation 7. If one accepts a polynomial smoothing/interpolation formula to describe the course of BG(t), then it, too can be linearly inverted, as shown in the attached Appendix C.

Algorithmic Implementation

The above described mathematical model and equations can then be applied to the CGS readings for remedying the physiology time lag between IG(t) and BG(t) by predicting BG levels using CGS outputs. An exemplary procedure of the invention is presented in the flow chart of FIG. 6.

Figure 6:
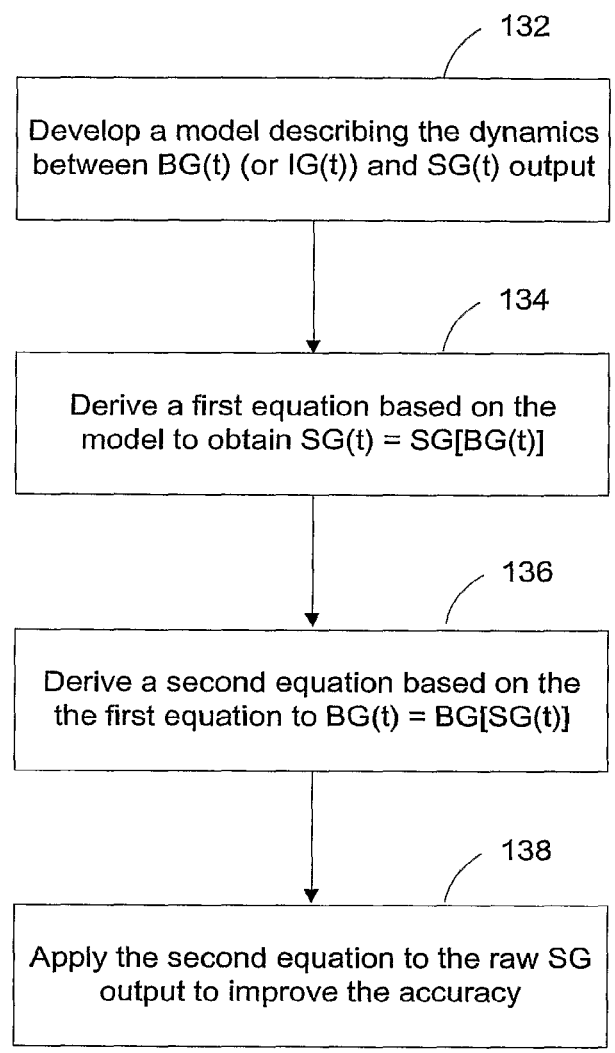
FIG. 6 is a flow chart showing the steps executed for improving the accuracy of the CGS using the time-lag correction method of the invention.

Referring to FIG. 6, the mathematical model as discussed above is developed at step 132. The model describes the dynamics among BG(t), IG(t), and CGS output SG(t). Based upon the model developed at step 132, the first mathematical equation is reduced so as to find out SG(t) as a function of BG(t) at step 134. This first equation is preferably developed using Fick's law of diffusion and Michaelis-Menten consumption. The first equation is then inversed so as to estimate the dynamics of BG(t) as a function of CGS output SG(t) at step 136. The inversed equation can then be applied to the CGS raw data to improve the accuracy of the CGS readings at step 138. An exemplary application of the inversed equation to the raw CGS data at step 138 is illustrated in FIG. 7.

Figure 7:
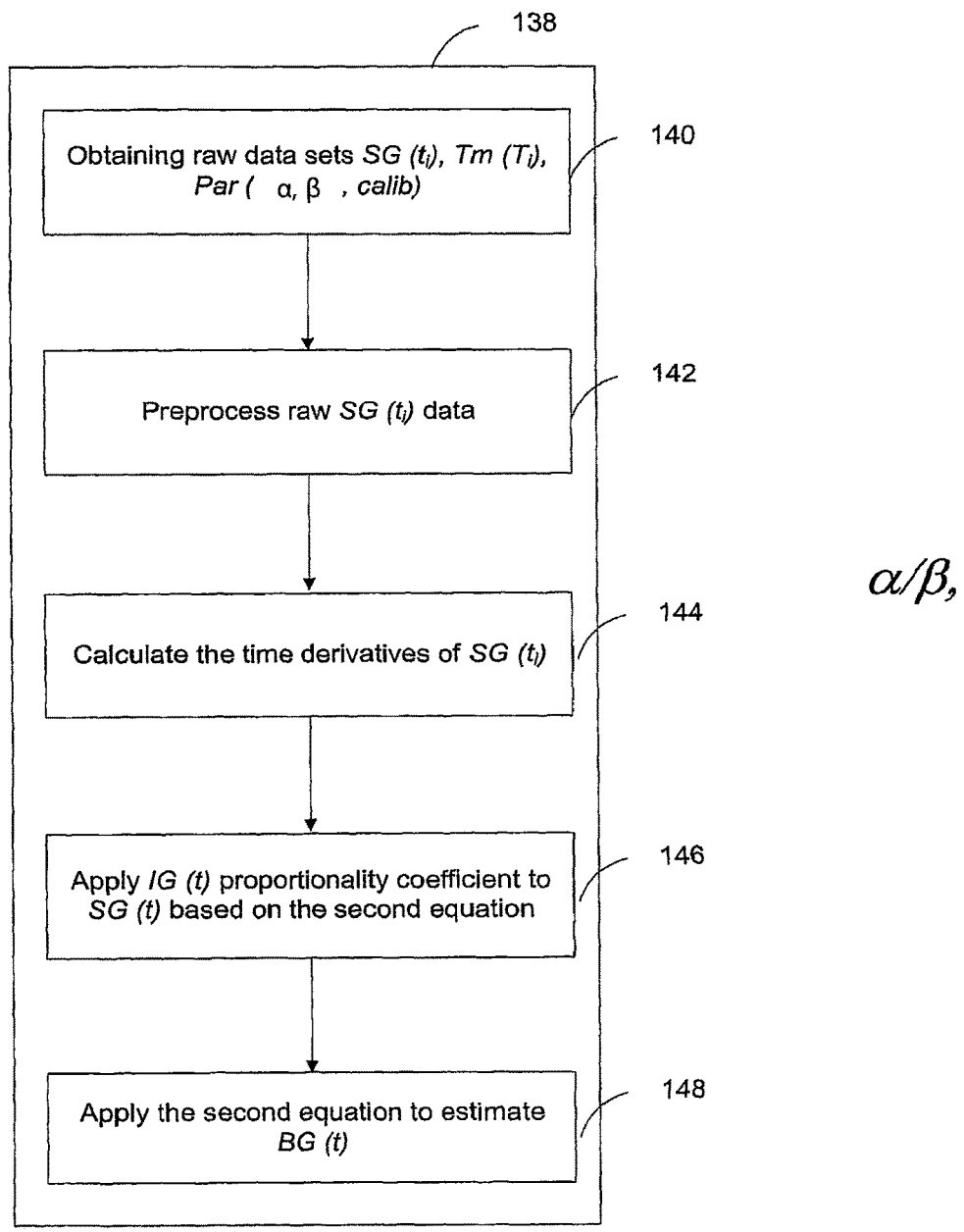
FIG. 7 is a flow chart showing the steps executed for calibrating the CGS according to yet another example of the invention.

Referring to FIG. 7, sets of raw data are obtained at step 140. The data sets comprise CGS outputs $SG(t_i)$, sample time $Tm(t_i)$, and parameters Par ($\alpha$, $\beta$, calib), wherein parameter calib is a parameter presented in equation 9 as calibration. The raw CGS data are preferably preprocessed (though not required) at step 142. Specifically, the CGS raw data are processed by initial regression and/or filtering to smooth CGS raw data. This step is important in that the investigation showed that the raw CGS data current suffer from noise and random spikes that need to be filtered out in order to improve the accuracy of the inverted model equation. There are many ways to regress and/or filter the CGS data. For example, the raw CGS data can be filtered based upon clinically observed BG rate-of-change in combination with a Bayesian estimation technique. In another example, the raw CGS output can be processed with Kalman filter based methods of equations 10 and 11 that produce optimal estimation with the assumption that the evolution of BG meets its limitations.

Given the pre-processed CGS data (or directly the raw CGS data without the above pre-processing), the rate of change (time derivative) of CGS output is calculated at step 144. A unique feature of the CGS output is the ability to estimate the derivative of their outputs. However, because of the observation and systematic noise and wandering sensor sensitivity, it is observed that such instant raw estimates are rarely optimal. Instead, a short-interval polynomial smoothing technique using exponential weights can produce better results, as indicated by experiments. Then the IG proportionality coefficients are applied to CGS at step 146, followed by application of the inverted model as described above to estimate the BG level at step 148.

Software Implementation

The process as described with reference to FIG. 7 can be implemented in many ways, one of which is in software. As an example, the above process can be implemented in a real-time version, which can be of particular usage for the application directly into CGS outputs so as to convert the raw CGS outputs into BG estimates, and produce real-time results. A set of real-time implementation program codes is attached herein as appendix D. Alternatively, the process can be implemented as a retrospective version that is of particular usage for performing retrospective improvement of CGS accuracy; and is applicable to CGS that do not display real-time data. A set of program codes for the retrospective implementation is attached herein as appendix E. It is noted that for ease of reference, the beginning of each line numbers is removed. A linearized version of the parameters is employed in favor of the computation speed. It will be appreciated by those skilled in the art that the program codes presented in appendices D and E are based on for demonstration purposes, and should not be interpreted as a limitation. Many other variations without departing from the spirit of the invention are also applicable.

Testing of the Method

The above described process for remedying the physiology time lag between BG and CGS output has been evaluated on data acquired during a study performed at the University of Virginia General Clinical Research Center (GCRC), which was an "add-on" project to ongoing NIH research grant (ROI DK 51562, Principal Investigator Boris Kovatchev). The add-on study was sponsored by Abbott Diabetes Care (P.I. William Clarke) to perform a direct comparison between two CGS: Abbott Navigator™ and Minimed CGMS. The development and testing of the model were among the objectives of the add-on study.

Subjects for the Study

Sixteen subjects with T1DM (11 male, 5 female, age 42 with standard deviation (SD) of 3 years, duration of diabetes 20 year with SD of 3 years. Informed consent was obtained from each. Subjects were admitted to the General Clinical Research Center in the evening prior to the study following a physical examination. A CGS system, the Freestyle Navigator™ was applied to each subject for approximately 12 hours prior to the initiation of the data recording, in accordance with the manufacturer's instructions and calibrated as recommended. All systems were inserted in the abdomen. No BG reference vs. CGS comparisons were made until the next morning. Study Protocol is defined as that identical hyperinsulinemic clamps were performed on two consecutive days:

On each day the hyperinsulinemic clamp used a constant insulin infusion rate of 40 m U/kg/min and variable glucose infusion rate to achieve and maintain BG levels at approximately 110 mg/dl. Subsequently, the glucose infusion rate was reduced to permit a controlled decline in BG levels of approximately 1 mg/dl/min until the BG level reached 40 mg/dl. The euglycemic clamp portion of the study varied in length from 70 to 210 minutes, while the duration of the BG reduction procedure ranged from 30 to 60 minutes. Arterialized blood was sampled every 5 minutes and reference BG levels were determined using a Beckman Glucose Analyzer (Beckman Instruments, Inc, Fullerton, Calif.). Freestyle Navigator™ glucose readings were recorded each minute and were synchronized with reference BG with a precision of 30 seconds. Reference and Navigator™ rates and direction of BG change were calculated at five-minute intervals. This procedure resulted in 29 clamp data sets for the 16 participants in the study.

Software Used for Analysis

Numerical analysis was conducted using R 2.1.1, which is an open-source free programming language and suite for statistic analysis (http//www.r-project.org). Beyond the base packages, the "odesolve," "fields," and "dsel" packages and their dependencies from CRAN repositories were used Microsoft Excel was used to produce graphs.

Results

Equation 12a was applied to the unfiltered Navigator™ raw data with parameters found via nonlinear least squares. Each data run begins at the start of descent into hypoglycemia. Table 1 presents a summary of the results for all 29 clamp events. It can be seen that the average RMS error of the Navigator™ was reduced more than 3-folds; and the %

RMS error was reduced more than 5-folds. In addition, the correlation between reference and sensor BG was improved by the model:

TABLE 1

|  | BG prediction using a method of the invention | Navigator™ |
|---|---|---|
| RMS error (mg/dl) | 8.1 | 27.3 |
| RMS % error | 10.6 | 55.1 |
| Pearson Correlation | 0.995 | 0.940 |

Figure 8:
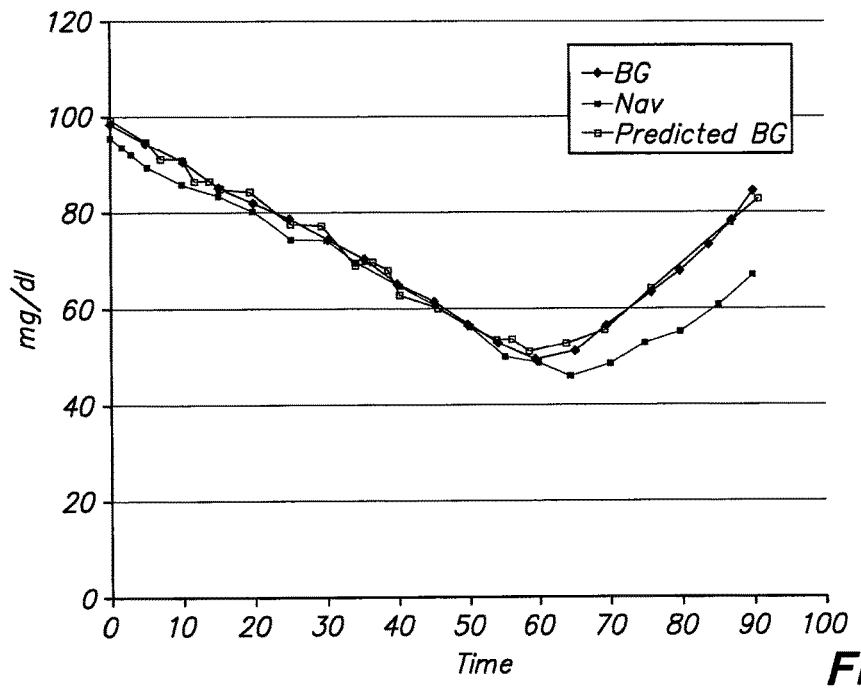
FIG. 8 is a diagram showing the improved CGS measurement using an exemplary method of the invention.
Figure 9:
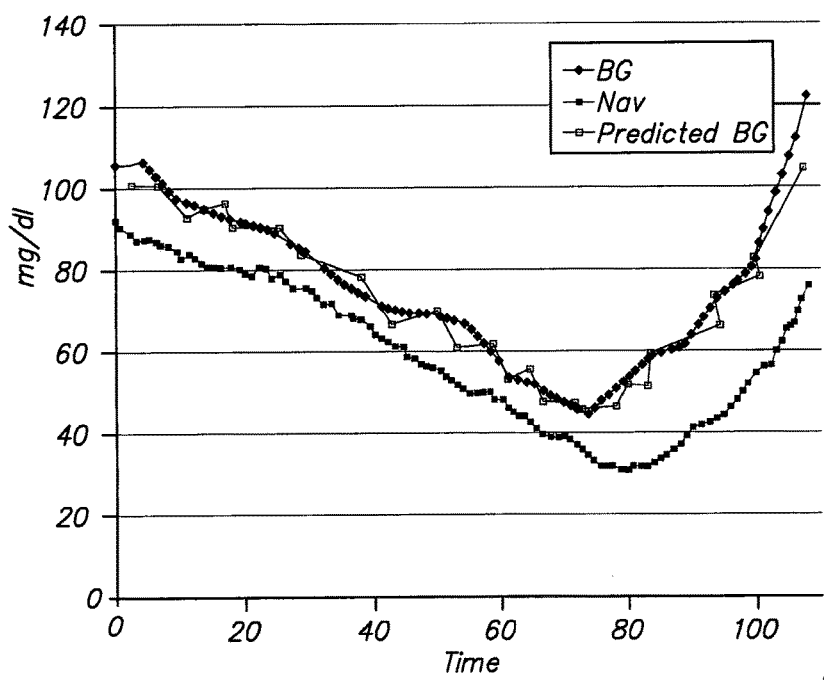
FIG. 9 is another diagram showing the improved CGS measurement using an exemplary method of the invention.
Figure 10:
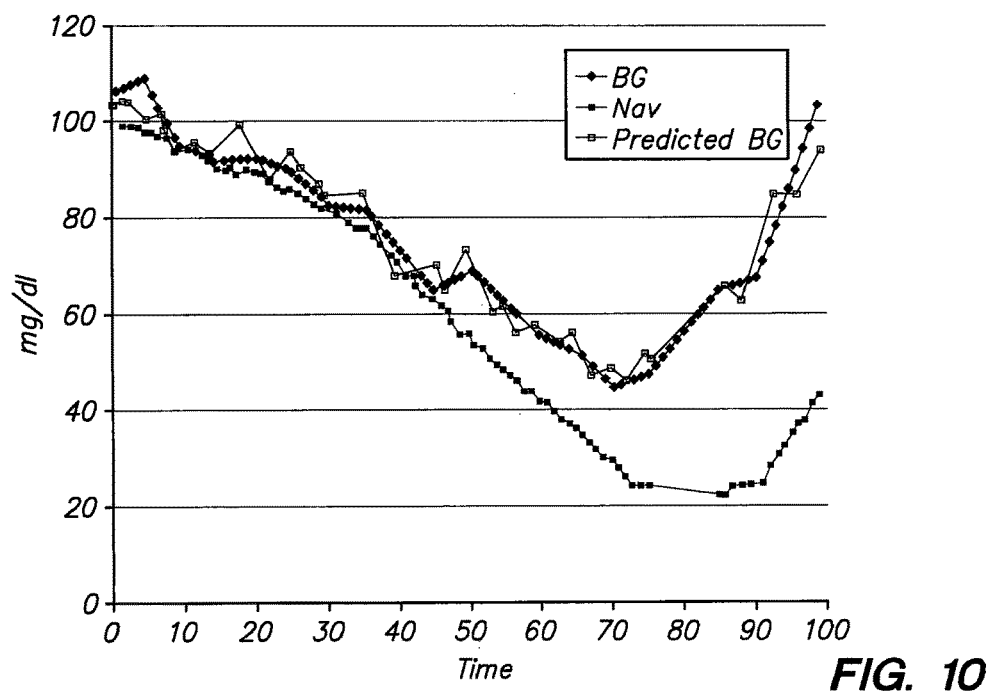
FIG. 10 is yet another diagram showing the improved CGS measurement using an exemplary method of the invention.

FIG. 8 to FIG. 10 depicts the results. Specifically, FIG. 8 shows the average of the 29 events matched at the nadir with five-minute data intervals. The solid diamond symbols are reference BG recorded by the Beckman analyzer. The solid squares are the data of the Navigator™. The open squares are the Navigator™ corrected by a method of the invention. It can be seen in the figure that the model-corrected data are much closer to reference BG than the original Navigator™ outputs. FIG. 9 and FIG. 10 show two individual patients with one-minute data intervals. In both cases, a correction of the Navigator™ data by a method of the invention (open squares) results in improved tracing of reference BG.

A Combined Accuracy Improvement Method and Device

Figure 11:
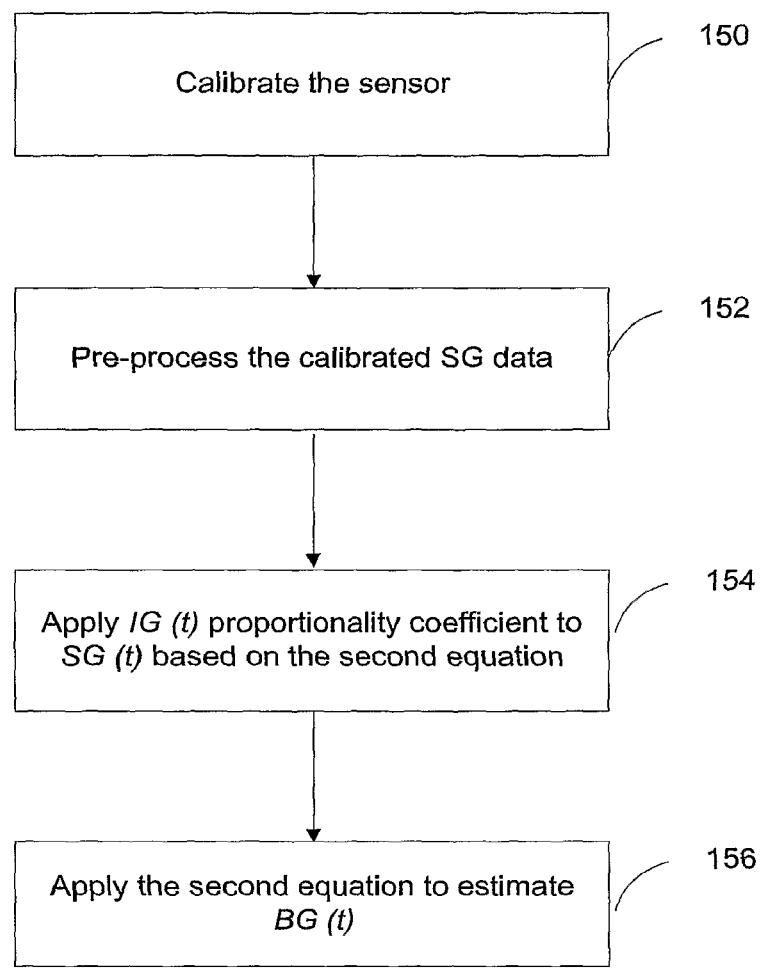
FIG. 11 is a flow chart showing the steps executed for improving the accuracy of the CGS according to yet another example of the invention.

As discussed above, the accuracy of the CGS output can be improved by an example of the invention through an improved calibration method. Alternatively, CGS accuracy can also be improved by remedying the physiology time lag between the BG and IG. In another example of the invention, the above two correction methods can be combined so as to further improve the CGS accuracy. FIG. 11 illustrates a flow chart for performing a combined accuracy improving process in accordance with another example of the invention.

Referring to FIG. 11, the combined process starts from calibrating the CGS using the method as described above with reference to FIGS. 4a-b. System errors can be eliminated or reduced. The CGS outputs from the calibrated CGS are preprocessed at step 152 by filtering and/or smoothing the calibrated CGS output. This step can be performed using the same or different method as described at step 142 in FIG. 7. It is noted that this step, though preferred, is not required. From the pre-process, sensor noise and/or minor random fluctuations in the CGS outputs and the first order time derivative can be removed or reduced. The first order time derivations of CGS outputs $SG(t_i)$ are calculated at step 144. The IG proportionality coefficient are then applied to the CGS outputs followed by the application of the inverted model equations to estimate the BG level, as described with reference to FIG. 6, which will not be repeated herein.

Table 2 shows the accuracy improvement using the methods according to example of the invention by comparing the CGS outputs obtained from the methods of the invention and the CGS outputs in a typical CGS in the art without employing the methods of the invention. The CGS outputs obtained from the typical CGS in the art are referenced in "Evaluating the accuracy of continuous glucose monitoring sensors: continuous glucose error grid analysis illustrated by therasense freestyle navigator data," by B Kovatchev, L Gonder Frederick, D Cox, and W Clarke, *Diabetes Care*, vol. 27, pp 1922-1928, 2004.

TABLE 2

CG_EGA Accuracy Results

| Zone | Accuracy % | Benign % | Error % | MAE mg/dl | MAPE % | N |
|---|---|---|---|---|---|---|
| Panel A: Original calibration | | | | | | |
| Hypoglycemia | 50 | 0 | 50 | 27.9 | 50.1 | 376 |
| Euglycemia | 96.4 | 0.2 | 3.4 | 20.4 | 22.6 | 532 |
| Panel B: d = 30 mg/dl calibration | | | | | | |
| Hypoglycemia | 86.7 | 4.8 | 8.5 | 10.9 | 19.8 | 376 |
| Euglycemia | 93.4 | 2.6 | 3.9 | 13.6 | 14.9 | 532 |
| Panel C: BG and SG (CGS output) compensation | | | | | | |
| Hypoglycemia | 100 | 0 | 0 | 4.9 | 8.4 | 376 |
| Euglycemia | 99.4 | 0.6 | 0 | 7.9 | 8.4 | 532 |

Panel A of Table 2 presents the continuous glucose error-grid analysis (CG-EGA) of the accuracy of Minimed CGMS™ during the clamp study described above, stratified by hypoglycemia and euglycemia. The clinically accurate sensor readings were 50.0% during hypoglycemia and 96.4% during euglycemia. The large difference between these percentages is primarily due to the more demanding clinical accuracy standards for hypoglycemia events: while for steady euglycemic state there is a large clinical tolerance for sensor errors. During clinically dangerous and rapidly developing conditions, such as hypoglycemia, the sensor is desired to meet higher standards in order to provide accurate feedback for appropriate and timely treatment decision. The CG-EGA reflects this distinction. Further, the MAE and the mean absolute percent error (MAPE) are included in Table 1 and stratified by BG range as well.

The panel B in Table 2 presents the CG-EGA, MAE and MAPE of a sensor re-calibrated by two reference BGs that are 30 mg/dl apart (e.g. differential d is 30 mg/dl), which is a clinically reasonable differential in the studied BG range. It can be seen that the percent of CG-EGA accurate readings increases from 50% to 86.7%, while MAE is reduced from 27.9 to 10.9 mg/dl during hypoglycemia. Improvement in MAE and MAPE is observed during euglycemia as well.

The panel C of Table 2 presents the CG-EGA, MAE and MAPE of the SIG vs. BG estimated after sensor re-calibration. It can be seen that the "accuracy" of SIG following BG fluctuation is high—nearly 100%, which signifies an excellent theoretical limit for potential sensor accuracy.

Examples of the invention can be implemented in many ways. For example, it can be implemented as a functional member of a continuous glucose sensor, or can be implemented as a standalone module associated with the continuous glucose sensor. In either instance, examples of the invention can be implemented as a set of program codes of software installed in a computing device, or a set of computer-executable codes of a hardware device coupled to the continuous glucose sensor. Regardless the implementation media, example of the invention can be associated with individual continuous glucose sensors for improving the accuracy of the individual glucose sensors. Alternatively, examples of the invention can be implemented in such a way that the real-time CGS data, along with related errors and error correction parameters and data, can be transmitted to an error processing center. The transmission may or may not be with the glucose data. In this way, a generalized continuous glucose sensing system can be established.

Figure 12:
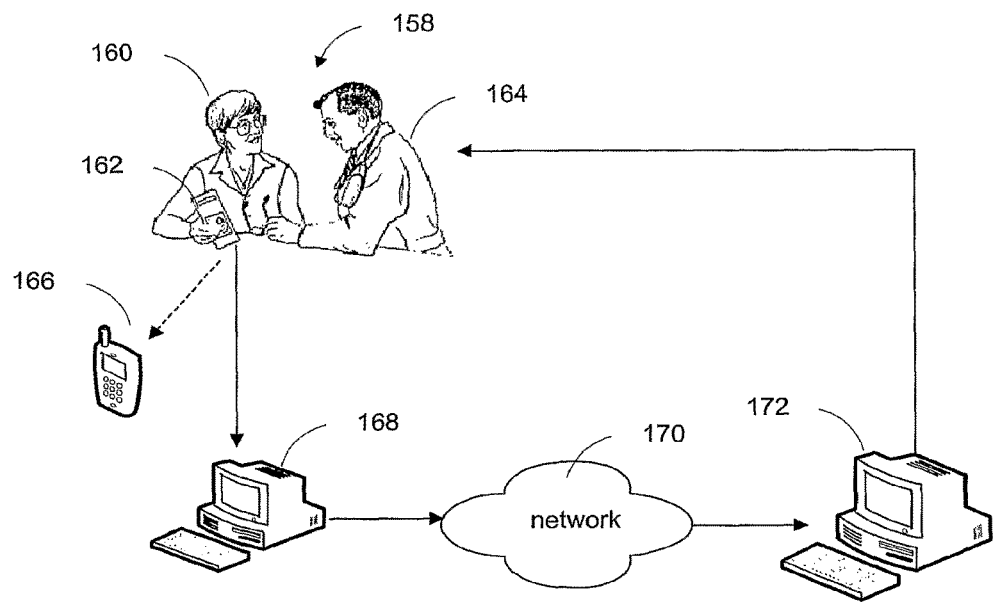
FIG. 12 is a diagram illustrating a system in which examples of the invention can be implemented.

FIG. 12 diagrammatically illustrates an exemplary system in which examples of the invention can be implemented. Referring to FIG. 12, clinic setup 158 provides a place for doctors (e.g. 164) to diagnose patients (e.g. 160) with diseases related with glucose. Continuous glucose sensor (or sensing device incorporating glucose testing function) 162 can be used to monitor and/or test the glucose levels of the patient. Such monitor and/or test can be short term (e.g. clinical visit) or long term (e.g. clinical stay or family). The continuous glucose sensor incorporates therein an example of the accuracy improvement methods as discussed above. The CGS outputs with improved accuracy can be used by the doctor for appropriate actions, such as insulin injection or food feeding for the patient, or other appropriate actions. Alternatively, the CGS output with improved accuracy can be delivered to computer terminal 168 for instant or future analyses. The delivery can be through cable or wireless or any other suitable medium. The CGS output with improved accuracy from the patient can also be delivered to a portable device, such as PDA 166. The CGS outputs with improved accuracy can be delivered to a glucose monitoring center 172 for processing and/or analyzing. Such delivery can be made accomplished through many ways, such as network connection 170, which can be wired or wireless.

In addition to the CGS outputs with improved accuracy, errors, parameters for accuracy improvements, and any accuracy related information can be delivered, such as to computer 168, and/or data processing center 172 for performing error analyses. This can provide a centralized accuracy monitoring and/or accuracy enhancement for glucose centers, due to the importance of the glucose sensors.

Figure 13:
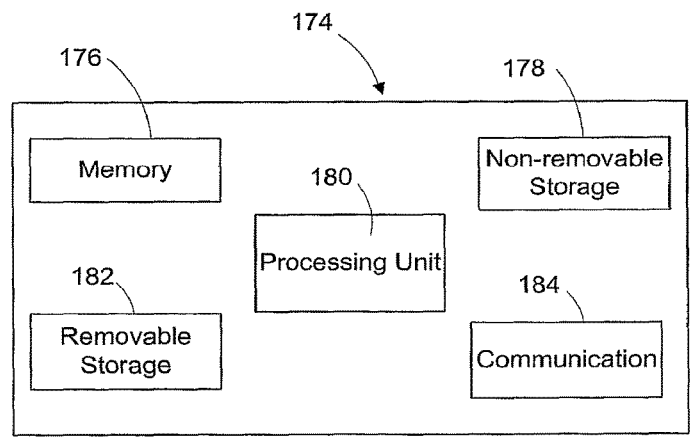
FIG. 13 is a diagram showing an exemplary computing device having computer-readable instructions in which example of the invention can be implemented.

As discussed earlier, examples of the invention can also be implemented in a standalone computing device associated with the target continuous glucose sensors. An exemplary computing device in which examples of the invention can be implemented is schematically illustrated in FIG. 13. Although such devices are well known to those of skill in the art, a brief explanation will be provided herein for the convenience of other readers.

Referring to FIG. 13, in its most basic configuration, computing device 174 typically includes at least one processing unit 180 and memory 176. Depending on the exact configuration and type of computing device, memory 176 can be volatile (such as RAM), non-volatile (such as ROM, flash memory, etc.) or some combination of the two.

Additionally, device 174 may also have other features and/or functionality. For example, the device could also include additional removable and/or non-removable storage including, but not limited to, magnetic or optical disks or tape, as well as writable electrical storage media. Such additional storage is shown in the figure by removable storage 182 and non-removable storage 178. Computer storage media includes volatile and nonvolatile, removable and non-removable media implemented in any method or technology for storage of information such as computer readable instructions, data structures, program modules or other data. The memory, the removable storage and the non-removable storage are all examples of computer storage media. Computer storage media includes, but is not limited to, RAM, ROM, EEPROM, flash memory or other memory technology, CDROM, digital versatile disks (DVD) or other optical storage, magnetic cassettes, magnetic tape, magnetic disk storage or other magnetic storage devices, or any other medium which can be used to store the desired information and which can be accessed by the device. Any such computer storage media may be part of, or used in conjunction with, the device.

The device may also contain one or more communications connections 184 that allow the device to communicate with other devices (e.g. other computing devices). The communications connections carry information in a communication media. Communication media typically embodies computer readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. As discussed above, the term computer readable media as used herein includes both storage media and communication media.

It will be appreciated by those of skill in the art that a new and useful method for improving accuracy of continuous glucose sensing devices and system using the same have been discussed herein. In view of the many possible embodiments to which the principles of this invention may be applied, however, it should be recognized that the embodiments described herein with respect to the drawing figures are meant to be illustrative only and should not be taken as limiting the scope of invention. Those of skill in the art will recognize that the illustrated embodiments can be modified in arrangement and detail without departing from the spirit of the invention. Therefore, the invention as described herein contemplates all such embodiments as may come within the scope of the following claims and equivalents thereof.

APPENIDX A

Subject matter of the following publications and US provisional application are incorporated herein by reference in entirety 1. Santiago J V: Lessons from the Diabetes Control and Complications Trial. *Diabetes* 1993, 42 1549-1554
2. B. Feldman, R B~azgS, Schwartz, and R. Weinstein, "A continuous glucose sensor based on wired enzyme technology and results from a 3 day trial in patients with type 1 diabetes," *Diabetes Technol Ther*, vol 5, pp 769-778, 2003
3. D Klonoff, "Continuous glucose monitoring: Roadmap for 21st century diabetes therapy," *Diabetes Care*, vol 28, pp 1231-1239, 2005
4. E Cheyne, D. Cavan, and D. Kerr, "Performance of continuous glucose monitoring system during controlled hypoglycemia in healthy volunteers," *Diabetes Technol Ther*, vol 4, pp 607-613, 2002
5. M Boyne, D Silver, J. Kaplan, and C. Saudek, "Timing of changes in interstitial and venous blood glucose measured with a continuous subcutaneous glucose sensor;" *Diabetes*, vol 52, pp 2790-2794, 2003
6. P T Stout, J R. Racchini, and M. E Hilgers, "A novel approach to mitigating the physiological lag between blood and interstitial fluid glucose measurements," *Diabetes Technol Ther*, vol. 6, pp. 635-644, 2004
7. E. Kulcu, J. Tamada, G. Reach, R Potts, and M. Lesho, "Physiological differences between interstitial glucose and blood glucose measured in human subjects," *Diabetes Care*, vol 26, pp 2405-2409, 2003
8. A Schoonen and K Wientjes, "A model for transport of glucose in adipose tissue to a microdialysis probe," *Diabetes Technol Ther*, vol. 5, pp. 589-598, 2003
9. G. M Steil, K Rebrin, F Hariri, S Jinagonda, S Tadros, C Darwin, and M F Saad, "Interstitial fluid glucose dynamics during insulin induced hypoglycaemia," *Diabetologia*, vol 48, pp. 1833-1840, 2005
10. K Rebrin and G Steil, "Can interstitial glucose assessment replace blood glucose measurements?" *Diabetes Technol Ther*, vol. 2, pp. 461472, 2000
11. Kovatchev, L Gonder Frederick, D Cox, and W Clarke, "Evaluating the accuracy of continuous glucose monitoring sensors: continuous glucose error grid analysis illustrated by therasense freestyle navigator data," *Diabetes Care*, vol. 27, pp 1922-1928, 2004
12. W Clarke, D. Cox, L Gonder Frederick, W Carter, and S Pohl, "Evaluating clinical accuracy of systems for self-monitoring of blood glucose," *Diabetes Care*, vol. 10, pp 622-628.1987
13. Hanefeld M: Postprandial hyperglycemia: noxious effects on the vessel wall *International Journal of Clinical Practice,* 2002, Supplement 129: 45-50
14. Esposito K, Giugliano D, Nappo F, Martella K, for the Campanian Postprandial Hyperglycemia Study Group. *Circulation*, 2004, 110: 214-219
15. Quagliaro L, Piconi L, Assalone R, Martinelli L, Motz E, Ceriello A: Intermittent 1-High Glucose Enhances Apoptosis Related to Oxidative Stress in Human Umbilical Vein Endothelial Cells: The Role of protein Kinase C and NAD(P)H-Oxidase Activation Diabetes, 2003, a: 2795-2804.
16. Van der Does F E. De Neeling J N, Snoek F J, Kostense P I, Grootenhuis P A, Bouter L M, and R J Heine: Symptoms and well-being in relation to glycemic control in type 1 diabetes, *Diabetes Care,* 1996, u: 204-210
17. De Sonnaville J J. Snoek F J Colly L P, Deville W. Wijkel D Heine R J: Well-being and symptoms in relation to insulin therapy in type 2 diabetes. *Diabetes Care,* 1998, a:919-24
18. Cox D J, Gonder-Frederick L A, McCall A, et al The effects of glucose fluctuation on cognitive function and QOL: the functional costs of hypoglycaemia and hyperglycaemia among adults with type 1 or type 2 diabetes *International Journal of Clinical Practice,* 2002, Supplement 129: 20-26
19. Hirsh I B, Brownlee M: Should minimal blood glucose variability become the gold standard of glycemic control? J Diabetes *Complications,* 2005, D: 178-181
20. Reichard P, Phil M Mortality and treatment side effects during long-term intensified conventional insulin treatment in the Stockholm Diabetes Intervention study Diabetes 43:313-317, 1994
21. The Diabetes Control and Complications Trial Research Group The effect of intensive treatment of diabetes on the development and progression of long-term complications of insulin-dependent diabetes mellitus N Engl J Med 329: 978-986, 1993
22. Gross™, Bode B W, Einhorn D, Kayne D M, Reed I H, White N H, Masttototaro J J: Performance evaluation of the MiniMed continuous glucose monitoring system during patient home use Diabetes Technol Ther. 2000; 2:49-56
23. Tavris D R, Shoaibi A: The public health impact of the MiniMed Continuous Glucose Monitoring System (CGMS): an assessment of the literature Diabetes Technol Ther 2004; 6:518-522
24. Chico A, Vidal-Rios P, Subiia M, Novials A: The continuous glucose monitoring system is useful for detecting unrecognized hypoglycemias in patients with type 1 and type 2 diabetes is not better than frequent capillary glucose measurements but is useful for improving metabolic control *Diabetes Care* 26:1153-1157, 2003
25. Mastrototaro J: The MiniMed Continuous Glucose Monitoring System (CGMS). J Pediatr Endocrinol Metab 12:751-758, 1999
26. Feldman B, Brazg R, Schwartz S, Weinstein R: A continuous glucose sensor based on wired enzyme technology—results from a 3-day trial in patients with type 1 diabetes Diabetes Technol Ther 2003; 5(5):769-79
27. Pickup J: Sensitive glucose sensing in diabetes Lancet 355:426-427, 2000
28. Gerritsen M, Jansen J A, Lutterman J A: Performance of subcutaneously implanted glucose sensors for continuous monitoring Neth J Med 54:167-179, 1999
29. Boyne, Silver, Kaplan, & Saudek: Timing of Changes in Interstitial and Venous Blood Glucose Measured With a Continuous Subcutaneous Glucose Sensor Diabetes 52: 2790-2794, 2003
30. Philip J Stout, Joel R Racchini, Michael E Hilgers: A Novel Approach to Mitigating the Physiological Lag Between Blood and Interstitial Fluid Glucose Measurements Diabetes Technol Ther 2004 6:5, 635-644
31. Schoonen & Wientjes: A Model for Transport of Glucose in Adipose Tissue to a Microdialysis Probe Diabetes Technol Ther 2003 5:4, 589-59%
32. A S Popel Analysis of capillary-tissue diffusion in multicapillary systems Mathematical Biosciences, 39: 187-211, 1978
33. G. M. Steil, K. Rebrin, F Hariri, S Jinagonda, S Tadros, C Darwin and M F Saad, Interstitial fluid glucose dynamics during insulin-induced hypoglycaemia Diabetologia 48:7, published online. DOI: 10.1007/s00125-, 005-1852-x
34. Zierler K: Whole body glucose metabolism Am J Physiol 276:E409-E426, 1999
35. Palfreyman R W, Clark A E, Denton R M, Holman G D, Kozka I S: Kinetic resolution of the separate GLUT1 and GLUT4 glucose transport activities in 3T3-L1 cells Biochem J. 284:275-, 282, 1992
36. Stengel R F: Optimal Control and Estimation New York: Dover Publications, 1994
37. Knobbe E J, Buckingham B: The extended Kalman filter for continuous glucose monitoring Diabetes Technol Ther 2005; 7:15-27
38. Palerm Cesx C., Willis John P., Desemone James, Bequette B Wayne: Hypoglycemia Prediction and Detection Using Optimal Estimation Diabetes Technol Ther 2005; 7:3-14,
39. G M Steil, K Rebrin, F Hariri, S Jinagonda, S Tadros, C Darwin and M F. Saad, Interstitial fluid glucose dynamics during insulin-induced hypoglycaemia Diabetologia 48:7, published online. DOI: 101007/s00125-005-1852-x"
40. International Patent Application Serial No. PCTiUS20051013792, entitled "Method, System and Computer. Program Product for Evaluating the Accuracy of Blood Glucose Monitoring SensorsiDevices, 11 filed Apr. 21, 2005
41. U.S. provisional application Ser. No. 60/815,191 to Kovatchev et al. filed Jun. 20, 2006

APPENDIX B—KALMAN RECURSION

Appendix A: Kalman Recursions

If we assume that our claim follows a system of the form A1.1, where x is a hidden system state vector, y is an observation vector, $w_s$ is system twin with covariance matrix Q, $w_o$ is observation noise with covariance matrix R, and the F, G, H matrices define system transitions, than the system is said to be a state space model.

$$x_{i+1} = Fx_i + Gz_i + w_s$$

$$y_i = Hx_i + w_o \qquad (A1.1)$$

The Kalman filter is a two step process. First, one-step-ahead predictions are made. Second, a correction to that prediction is made based upon new measurements. Let us introduce to notation of $\hat{x}_{i,j}$ meaning "the estimate of x at i given the measurements up to and including j." Assuming that we have current estimates of x and the error covariance of that estimate, P, we can write the first step as A1.2. In order to correct the estimates, we then calculate the Kalman gain in A1.3, and update the estimates in A1.4 using the new measurement, y.

$$\hat{x}_{i,j-1} = F\hat{x}_{i-1|i-1} + G\hat{z}_{i-1}$$

$$\hat{P}_i = FP_{i-1}F^T + Q \qquad (A1.2)$$

$$K_i = \hat{P}_i H^T (H\hat{P}_i H^T + R)^{-1} \qquad (A1.3)$$

$$\hat{x}_{i,j} = \hat{x}_{i,j-1} + K_j(y_j - H\hat{x}_{i,j-1})$$

$$P_i = (I - K_i H)\hat{P}_i \qquad (A1.4)$$

APPENDIX B—RECURSION PROCESS $$X\tilde{I} = |BG_{i,interpj}| \qquad (A2.7)$$

$$\text{diagonal}(X^*\tilde{I}) = B^k G \qquad (A2.8)$$

The diagonal operator can be written as in A2.9, which reduces A2.8 to A2.10. Furthermore, by again concatenating the first q+1 column vectors we can form the desired matrix A2.1 in A2.11.

$$A2.9) \quad C_i \equiv \{C[ii] = 1, \text{else } C[ij] = 0\}, \text{diagonal}(A) = \sum_{j=1}^{n} C_j A e_i^T$$

$$A2.10) \quad \overset{k}{BG} = \left\{ \sum_{i=1}^{n} C_i \overset{k}{X}(X^T W_i X)^{-1} X^T W_i \right\} BG, \{\ldots\} \cong M_\kappa$$

$$A2.11) \quad \tilde{BG} = \sum_{\kappa=0}^{q} M_k BG e_\kappa$$

Finally, by inserting A2.11 into A2.3 we arrive at A2.12, a linear system which can be solved by methods such as QR decomposition.

$$A2.12) \quad f(t) + \alpha/\beta = \left\{ (I - \delta B_s) \sum_{k=0}^{q} M_\kappa (-1/\beta)^\kappa \right\} BG$$

APPENDIX D—PROGRAM CODES OF REAL-TIME IMPLEMENTATION

Version 1: Real-Time Application:

```
1 GetNewBGPreds <- function(Nav,times,par) {
#needs times in minutes to make the parameters work right
#remove missing values
2 times[!is..na(Nav)]->times;Nav[!is.na(Nav)l->Nav;
#second apply the calibration parameter
3 Navipar [ [ 31 ] ->Nav;
#third, create arrays to hold estimates of IG, and dot IG
4 rep(O., times=length(Nav))->Idot; Nav->IG;
#fourth, create estimates of dot IG in the time before much data has been collected
5 (IG[2]-IG[ll) /(times [Zl-times ill) ->Idot 121 ;
6 #linear interpolation
7 data frame(y=IG[l:3] ,x=times[l: 31 )->td;
8 lm(y-x,data=td)- >tx;t xScoefficients [2]- >tx;attr
(tx," names")< -NULL; tx->Idot [3] ;
9 data frame (y=IG[l:4] ,x=times [1:4])->td;
10 lm(y-x,data=td) ->tx;tx$coefficients [2]->tx;attr
(tx, "namesw)<-NULL; tx->Idot [4] ;
#fifth, create estimates using splines over the CGS data
11 for (i in S:length(Nav)) (
12 times [ (i-4) : (i) ] ->tt;Nav[ (i-4) : (i) 1 ->td;
13 smooth spline(x=tt,y=td,df=l)->temp;
14 predict (temp,t imes [i] ,deriv=1)$ y-2Idot [i];
15 predict (temp, times [1]) Sy->IG[il ;
16}
#sixth, apply the main fomula
17 IG+Idotkpar [ [2] ]+par [ [1] ] ->NewBG; #seventh, return the result
18 NewBG)
```

APPENDIX D—PROGRAM CODES OF RETROSPECTIVE IMPLEMENTATION

Version 2: Retrospective Correction:

In addition to the real-time implementation, one can introduce an artificial delay by extending the time over which each spline is interpolated in line 12 from "(i−4):(i)" to "(i−4):(i+4). 11 In purely retrospective analysis, one can use the more simple form given next.

```
19 GetOldBGPreds <- function(Nav,times,par) {
#eliminate missing values
20 times [ !is .na (Nav)] ->times;
21 Nav [ !is .na (Nav) 1 ->Nav;
#apply calibration parameter
22 par [ [3] 1 *Nav->Nav;
#create a smoothing spline regression over all the data
23 sreg (times, Nav) ->Navfit ;
#use it to predict IG
24 predict (Navfit,times)->IG;
#use it to predict dot IG
25 predict(N avfit, times,deriv=l)->Idot;
#apply main formula
26 (Idot) *par [ [2] ] +par [ [I] 1 +IG->BGpreds;
#return predictions
27 BGpreds)
```

Finally, if the full Michaelis-Menton form of the equation 3 is desired, then one can simply replaces "par [[1]] "with" par [[1]]*I G/(126.+IG)" in lines 17 and 27. R contains many other smoothing and interpolation facilities, and the use of sreg, smooth spline, and lm can be substituted with many of them, although the input/output format is frequently different.

What is claimed is:

1. A method for improving accuracy of a continuous glucose sensor (CGS), comprising:
   calibrating the CGS at a first time;
   dynamically monitoring a CGS value and a rate of CGS change over time;
   determining, at a second time, whether a first condition is met, wherein the first condition is met if an absolute value of the rate of CGS change at the second time is less than a first predetermined value, and wherein the absolute value of the rate of CGS change is an absolute value of a first order time derivative of the CGS value;

in response to the first condition not being met, maintaining the calibration of the CGS at the first time;

in response to the first condition being met, determining whether a second condition is met;

in response to a determination that the first condition and the second condition are met, calibrating the CGS at the second time.

2. The method of claim 1, wherein the first predetermined value is 1 mg/dL/time.

3. The method of claim 1, wherein determining whether the second condition is met comprises determining whether an absolute change between the CGS value at the second time and the CGS value at the first time is greater than a second predetermined value; and wherein the method further comprises, in response to a determination that the second condition is not met, maintaining the calibration of the CGS at the first time.

4. The method of claim 3, wherein the second predetermined value is at least 15 mg/dL.

5. The method of claim 3, wherein the second predetermined value is at least 20 mg/dL.

6. The method of claim 3, wherein the second predetermined value is at least 30 mg/dL.

7. The method of claim 3, wherein the second predetermined value is at least 40 mg/dL.

8. The method of claim 1, further comprising:

improving accuracy of a CGS output by remedying a physiology time lag between a blood glucose level and a glucose level in an interstitial fluid that interacts with the blood glucose.

9. The method of claim 8, wherein the step of improving accuracy of the CGS output further comprises:

deriving a mathematical equation describing a time dependence of the CGS output on the blood glucose level;

deriving the time dependence on the blood glucose level as a function of the CGS output; and applying the derived function to a set of CGS raw outputs so as to predict a blood glucose level at a later time to correct the CGS output.

10. The method of claim 9, wherein the mathematical equation is derived based on a model that includes a description of a diffusion interaction between the blood glucose and the glucose in the interstitial fluid.

11. The method of claim 9, wherein the mathematical equation is derived based on a model that includes a description of an assumption of the glucose in the interstitial fluid.

12. The method of claim 1, further comprising, in response to only the first condition being met, calibrating the CGS at the second time.

13. A method for improving the accuracy of a glucose sensor, comprising:

requesting and receiving a first blood glucose reference value when the glucose sensor measures a first in vivo glucose value;

calibrating the glucose sensor using the first blood glucose reference value and the first in vivo glucose value;

measuring, by the glucose sensor, a second in vivo glucose value and a rate of in vivo glucose change;

determining if an absolute rate of in vivo glucose change value is less than a first predetermined value;

determining if an absolute difference between the second in vivo glucose value and the first in vivo glucose value is greater than a second predetermined value;

in response to a determination that the absolute rate of in vivo glucose change value is less than the first predetermined value, and a determination that the absolute difference between the second in vivo glucose value and the first in vivo glucose value is greater than the second predetermined value, requesting and receiving a second blood glucose reference value; and calibrating the glucose sensor using the second blood glucose reference value and the second in vivo glucose value, wherein the absolute rate of in vivo glucose change value is based on a first order time derivative of the second in vivo glucose value.

14. A system for improving an accuracy of a glucose sensor, comprising:

at least one processing unit;

memory coupled to the at least one processing unit, wherein the memory is configured to store program modules and instructions comprising:

an accuracy improving module accessible to an output of the glucose sensor, further comprising:

a decision making mechanism capable of determining a calibration at a second time based upon at least one of a dynamically monitored output of the glucose sensor, wherein the decision making mechanism is configured to:

determine if an absolute rate of in vivo glucose change value at the second time is less than a first predetermined value, determine if an absolute difference between an in vivo glucose value at the second time and an in vivo glucose value at a first time is greater than a second predetermined value, and in response to a determination that the absolute rate is less than the first predetermined value, and the absolute difference is greater than the second predetermined value, calibrating the glucose sensor, wherein the absolute rate of in vivo glucose change value is based on a first order time derivative of the in vivo glucose value at the second time.

15. The system of claim 14, wherein the accuracy improving module further comprises:

an initial request module capable of initiating an initial calibration at a predetermined time sequence.

16. The system of claim 15, wherein the decision making mechanism further comprises:

a monitoring module capable of dynamically monitoring the output from the glucose sensor, wherein the output comprises an in vivo glucose value and a rate of in vivo glucose change.

* * * * *